(12) United States Patent
Micallef

(10) Patent No.: US 10,900,064 B2
(45) Date of Patent: Jan. 26, 2021

(54) METHOD FOR DETECTING NUCLEOSOMES CONTAINING NUCLEOTIDES

(75) Inventor: Jacob Vincent Micallef, London (GB)

(73) Assignee: Belgian Volition SPRL, Isnes (BE)

( * ) Notice: Subject to any disclaimer, the term of this patent is extended or adjusted under 35 U.S.C. 154(b) by 124 days.

(21) Appl. No.: 14/239,783

(22) PCT Filed: Aug. 31, 2012

(86) PCT No.: PCT/GB2012/052128
§ 371 (c)(1),
(2), (4) Date: Mar. 27, 2014

(87) PCT Pub. No.: WO2013/030577
PCT Pub. Date: Mar. 7, 2013

(65) Prior Publication Data
US 2014/0363812 A1    Dec. 11, 2014

Related U.S. Application Data

(60) Provisional application No. 61/530,295, filed on Sep. 1, 2011.

(30) Foreign Application Priority Data

Sep. 1, 2011  (GB) .................................. 1115095.0

(51) Int. Cl.
*C12Q 1/68*     (2018.01)
*C12Q 1/6804*   (2018.01)
*G01N 33/58*    (2006.01)

(52) U.S. Cl.
CPC .......... *C12Q 1/6804* (2013.01); *G01N 33/585* (2013.01); *G01N 2400/10* (2013.01)

(58) Field of Classification Search
USPC .......... 435/6.1, 6.11, 7.1, 7.2, 7.5, 91.1, 183; 436/94, 501; 536/23.1; 424/130.1, 178.1
See application file for complete search history.

(56) References Cited

U.S. PATENT DOCUMENTS

| | | | | |
|---|---|---|---|---|
| 6,329,179 B1 * | 12/2001 | Kopreski | ............ | C12Q 1/6806 435/6.11 |
| 6,630,301 B1 * | 10/2003 | Gocke | ................. | C12Q 1/6886 435/6.11 |
| 9,187,780 B2 * | 11/2015 | Micallef | .......... | G01N 33/57496 |
| 2007/0092509 A1 * | 4/2007 | Mittra | ................. | A61M 1/3472 424/140.1 |
| 2008/0064043 A1 | 3/2008 | Berlin et al. | | |
| 2008/0108094 A1 * | 5/2008 | Holdenrieder | ..... | G01N 33/5091 435/7.92 |
| 2008/0131954 A1 * | 6/2008 | Stone | ................ | C12N 15/1006 435/270 |
| 2009/0170796 A1 * | 7/2009 | Shi | ........................... | C12Q 1/26 514/44 R |
| 2009/0181373 A1 * | 7/2009 | Li | ....................... | C12Q 1/6853 435/6.12 |
| 2009/0208941 A1 | 8/2009 | Berlin et al. | | |
| 2013/0230858 A1 | 9/2013 | Cantor et al. | | |

FOREIGN PATENT DOCUMENTS

| | | |
|---|---|---|
| EP | 1 668 368 A1 | 6/2006 |
| FR | 2652901 | 4/1991 |
| WO | WO-99/47924 | 9/1999 |
| WO | WO-01/53834 A2 | 7/2001 |
| WO | WO-2005/003381 | 1/2005 |
| WO | WO-2005/019826 | 3/2005 |
| WO | WO-2005/040814 | 5/2005 |
| WO | WO-2007/050706 | 5/2007 |
| WO | WO-2007/076200 | 7/2007 |
| WO | WO-2008/130516 | 10/2008 |
| WO | WO-2009/115313 | 9/2009 |
| WO | WO-2010/057501 A1 | 5/2010 |
| WO | WO-2010/120942 | 10/2010 |
| WO | WO-2011/017677 A2 | 2/2011 |
| WO | WO-2011/131772 A1 | 10/2011 |
| WO | WO-2011/150974 A1 | 12/2011 |
| WO | WO-2011/157905 A1 | 12/2011 |
| WO | WO-2013/030577 A1 | 3/2013 |
| WO | WO-2013/030579 A1 | 3/2013 |
| WO | WO-2014/131841 A1 | 9/2014 |

OTHER PUBLICATIONS

Stollar et al., A recognition site on synthetic helical oligonucleotides for monoclonal anti-native DNA autoantibody. Proc. Natl. Acad. Sci. USA, 83, 4469-4473, 1986.*
Zhao et al., Heterochromatin Protein 1 Binds to Nucleosomes and DNA in Vitro. J. Biol. Chem., 275, 28332-28338, 2000.*
Inouye et al., Detection of Inosine-containing Transfer Ribonucleic Acid Species by Affinity Chromatography on Columns of AntI.Inosine Antibodies. J. Biol. Chem., 248, 8125-8129, 1973.*
Roloff et al., Comparative study of methyl-CpG-binding domain proteins. BMC Genomics. 4 (1), 1, 2003.*
Roloff et al., BMC Genomics. 4 (1), 1, 2003.*
Ball et al., "5-Methylcytosine is localized in nucleosomes that contain histone H1", PNAS, 1983, 80:5490-5494.
Barciszewska et al., "Analysis of 5-Methylcytosine in DNA of Breast and Colon Cancer Tissues", IUBMB Life, 2007, 59(12):765-770.

(Continued)

*Primary Examiner* — Frank W Lu
(74) *Attorney, Agent, or Firm* — McDermott, Will & Emery LLP; Judy M. Mohr; Brett A. Schweers

(57) ABSTRACT

The invention relates to a method for detecting and measuring the presence of mono-nucleosomes and oligo-nucleosomes and nucleosomes that contain particular nucleotides and the use of such measurements for the detection and diagnosis of disease. The invention also relates to a method of identifying nucleosome associated nucleotide biomarkers for the detection and diagnosis of disease and to biomarkers identified by said method.

4 Claims, 12 Drawing Sheets

(56) References Cited

OTHER PUBLICATIONS

Bennett et al., "Frequently Methylated Tumor Suppressor Genes in Head and Neck Squamous Cell Carcinoma", Cancer Res, 2008, 68(12):4494-4499.
Missaoui et al., "Global DNA Methylation in Precancerous and Cancerous Lesions of the Uterine Cervix", Asian Pacific J Cancer Prev, 2010, 11:1741-1744.
Parker et al., "The roles of translation initiation regulation in ultraviolet light-induced apoptosis", Molecular and Cellular Biochemistry, (2006), 293(1-2):173-181.
PCT International Search Report and Written Opinion for Appl. No. PCT/GB2012/052128, dated Feb. 11, 2013.
Zhu et al., "Use of DNA Methylation for Cancer Detection and Molecular Classification", J Biochem Mol Biol, 2007, 40(2):135-141.
Zukiel et al., "A Simple Epigenetic Method for the Diagnosis and Classification of Brain Tumors", Molecular Cancer Research, 2004, 2:196-202.
Epi proColon Physician Brochure, by epigenomics, 2017, http://www.epiprocolon.com/wp-content/uploads/sites/3/2017/06/MKT_0026_Physician_messaging_and_brochure_rev5.pdf.
Grutzmann et al., "Sensitive Detection of Colorectal Cancer in Peripheral Blood by Septin 9 DNA Methylation Assay", PLoS ONE, 2008, 3(11):e3759 (8 pages).
Ulz et al., "Inferring expressed genes by whole-genome sequencing of plasma DNA", Nature Genetics, 2016, 48:1273-1278.
Hatayama et al., Biochemistry International, vol. 9, pp. 251-258, 1984.
Huck et al., FASEB J, vol. 13, pp. 1415-1422, 1999.
Ko et al., Nature, vol. 468, pp. 839-843, 2010.
Munzel et al., Angew Chem Int Ed Engl, vol. 50, pp. 6460-6468, 2011.
Viens et al., Molecular and Cellular Biology, vol. 26, pp. 5325-5335, 2006.
Lin et al., Biophysical Journal, vol. 97, pp. 1804-1807, 2009.
Hung, et al., Eukaryotic Cell, vol. 2, No. 5, pp. 841-846, 2003.
Lister et al., "Human DNA methylomes at base resolution show widespread epigenomic differences", Nature, Nov. 19, 2009, vol. 462, No. 7271, pp. 315-322.
Malins et al., "Major Alterations in the Nucleotide Structure of DNA in Cancer of the Female Breast", Cancer Research, Oct. 1, 1991, vol. 51, pp. 5430-5432.
Nguyen et al., "DNA damage and mutation in human cells exposed to nitric oxide in vitro", Proc. Natl. Acad. Sci. USA, Apr. 1992, vol. 89, pp. 3030-3034.
Andersson,Ulf, and Harris,Helena Erlandsson, "The role of HMGB1 in the pathogenesis of rheumatic disease",Biochimica et Biophysica Acta, 1799., pp. 141-148, 2010.
Eggena, M. et al. (2000) "Identitication of Histone H1 as a Cognate Antigen of the Ulcerative Colitis-associated Marker Antibody pANCA," Journal of Autoimmunity 14:83-97.
Fujiya et al., "Nucleosomal DNA hypermethylation detected in sera of colon cancer patients as a marker of cancer surveillance", Digest Dis. Week Abs., 2003, Abstract No. W1331. (2 pages).
Fullgrabe et al., "Histone onco-modifications", Oncogene, 30(31), pp. 3391-3403, Aug. 2011.
Gabler et al., "Extranuclear detection of histones and nucleosomes in activated human lymphoblasts as an early event in apoptosis", Annals of the Rheumatic Diseases, 2004, 63(9):1135-1144.
Hergeth et al., "The H1 linker histones: multifunctional proteins beyond the nucleosomal core particle", EMBO Reports, 2015, 16(11):1439-1453.
Hock et al., TRENDS in Cell Biology, vol. 17, No. 2, pp. 72-79.
Holdenreider et al., "Nucleosomes in Serum of Patients With Benign and Malignant Diseases", Int. J. Cancer, 2001, 95:114-120.
Holdenrieder et al., "Clinical use of circulating nucleosomes", Critical Reviews in Clinical Laboratory Sciences United States, 2009, 46(1):1-24.
Izzo & Schneider, "The role of linker histone H1 modications in the regulation of gene expression and chromatin dynamics", BBA Gene Regulatory Mechanisms, 2016, 1859:486-495.
Louie, M. et al., "Androgen-induced recruitment of RNA polymerase II to a nuclear receptor-p160 coactivator complex," PNAS, vol. 100, No. 5, pp. 2226-2230 (Mar. 2003).
Scaffidi, Paola, "Histone H1 alterations in cancer", Biochemica et Biophysica Acta, 2016, 1859(3):533-539.
Sun, Lee et al., "Interactions between glucocorticoid receptor-bearing chromatin and antireceptor antibody preparations," J. Steroid. Biochem., vol. 26, No. 1, pp. 83-92 (1987).
Tang et al., Biochim. Biophys. Acta., vol. 1799, pp. 131-140.
Urbonaviciute, V. And Voll, R.E., "High-mobility group box 1 represents a potential marker of disease activity and novel therapeutic target in systemic lupus erythematosus", J. Internal Medicine,vol. 270, pp. 1365-2796, Oct. 2011.
Urbonaviviute et al., "Induction of inflammatory and immune responses by HMGB1-nucleosome complexes: implication for the pathogenesis of SLE", J. Exp. Med., 205(13):3007-3018, 2008.

\* cited by examiner

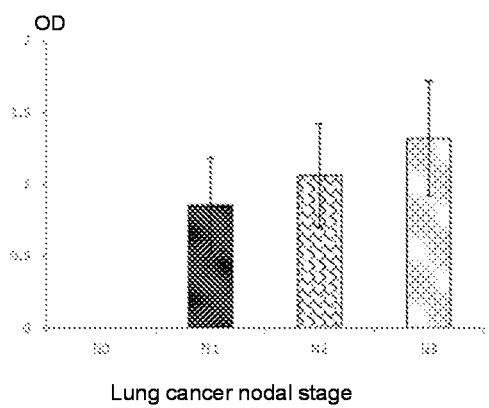

Lung cancer nodal stage

N0 No regional lymph node metastases
N1 Metastasis in ipsilateral peribronchial and/or
   ipsilateral hilar lymph nodes and intrapulmonary
   nodes, including involvement by direct extension
N2 Metastasis in ipsilateral mediastinal
   and/or subcarinal lymph node(s)
N3 Metastasis in contralateral mediastinal,
   contralateral hilar, ipsilateral or contralateral scalene,
   or supraclavicular lymph node(s)

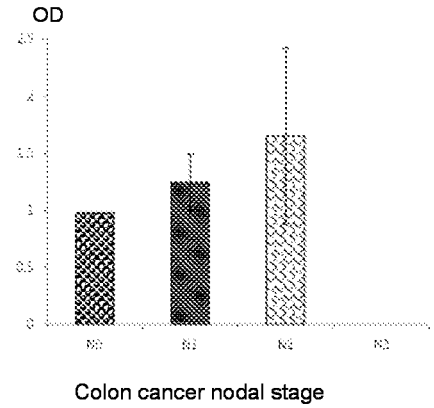

Colon cancer nodal stage

N0 No regional lymph node metastasis
N1 Metastasis in 1–3 regional lymph nodes
N2 Metastasis in 4 or more regional lymph nodes

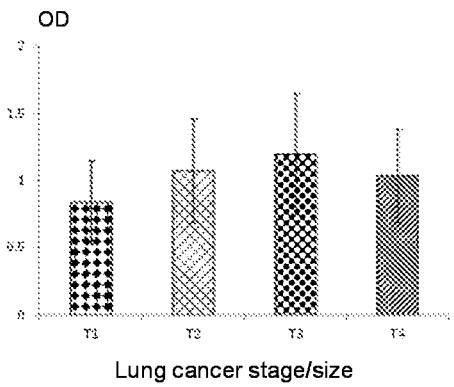

Lung cancer stage/size

T1: tumor <3cm
T2: 3cm < tumor < 7cm
T3: tumor > 7 cm
T4: tumor of any size that invades
    other organ, tissue

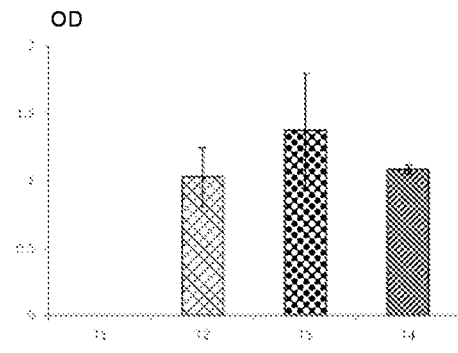

Colon cancer stage/size

T1: tumor invades submucosa
T2: tumor invades muscularis propria
T3: tumor invades through the muscularis propria
    into pericolorectal tissues
T4: tumor penetrates surface of the visceral peritoneum,
    invades or is adherent to the other organs or structures

FIGURE 19

METHOD FOR DETECTING NUCLEOSOMES CONTAINING NUCLEOTIDES

CROSS-REFERENCE TO RELATED APPLICATIONS

This application is the U.S. national stage application of International Patent Application No. PCT/GB2012/052128, filed on Aug. 31, 2012, which claims priority to GB Application No. 1115095.0, filed on Sep. 1, 2011, and U.S. Provisional Application No. 61/530,295, filed on Sep. 1, 2011, each of which is incorporated herein by reference in its entirety.

FIELD OF THE INVENTION

The invention relates to a method for detecting and measuring the presence of mono-nucleosomes and oligo-nucleosomes and nucleosomes that contain particular nucleotides and the use of such measurements for the detection and diagnosis of disease. The invention also relates to a method of identifying nucleosome associated nucleotide biomarkers for the detection and diagnosis of disease and to biomarkers identified by said method.

BACKGROUND OF THE INVENTION

The human body comprises several hundred cell types. All of these cell types contain the same genome but have widely different phenotypes and different functions in the body. This phenotypic diversity is due to the differential expression of the genome in different cell types. The control of differential gene expression is not entirely understood but the basic mechanisms include gene regulation by a number of interconnected epigenetic signals associated with the gene, including control of the chromatin packing as euchromatin or heterochromatin, control of nucleosome positioning and nuclease accessible sites, methylation, hydroxymethylation and other modifications of DNA and variation in the structure of the nucleosomes around which the DNA is wrapped.

The nucleosome is the basic unit of chromatin structure and consists of a protein complex of eight highly conserved core histones (comprising a pair of each of the histones H2A, H2B, H3 and H4). Around this complex is wrapped approximately 146 base pairs of DNA. Another histone, H1 or H5, acts as a linker and is involved in chromatin compaction. The DNA is wound around consecutive nucleosomes in a structure often said to resemble "beads on a string" and this forms the basic structure of open or euchromatin. In compacted or heterochromatin this string is coiled and super coiled into a closed and complex structure (Herranz and Esteller, 2007).

The structure of nucleosomes can vary by Post Transcriptional Modification (PTM) of histone proteins and by the inclusion of variant histone proteins. PTM of histone proteins typically occurs on the tails of the core histones and common modifications include acetylation, methylation or ubiquitination of lysine residues as well as methylation of arginine residues and phosphorylation of serine residues and many others. Histone modifications are known to be involved in epigenetic regulation of gene expression (Herranz and Esteller, 2007). The structure of the nucleosome can also vary by the inclusion of alternative histone isoforms or variants which are different gene or splice products and have different amino acid sequences. Histone variants can be classed into a number of families which are subdivided into individual types. The nucleotide sequences of a large number of histone variants are known and publicly available for example in the National Human Genome Research Institute NHGRI Histone DataBase (Mariño-Ramírez, L., Levine, K. M., Morales, M., Zhang, S., Moreland, R. T., Baxevanis, A. D., and Landsman, D. The Histone Database: an integrated resource for histones and histone fold-containing proteins. *Database* Vol. 2011. (Submitted) and http://genome.nhgri.nih.gov/histones/complete.shtml), the GenBank (NIH genetic sequence) DataBase, the EMBL Nucleotide Sequence Database and the DNA Data Bank of Japan (DDBJ).

Normal cell turnover in adult humans involves the creation by cell division of some $10^{11}$ cells daily and the death of a similar number, mainly by apoptosis. During the process of apoptosis, chromatin is broken down into mononucleosomes and oligonucleosomes which are released from the cells. Under normal conditions the levels of circulating nucleosomes found in healthy subjects is reported to be low. Elevated levels are found in subjects with a variety of conditions including many cancers, auto-immune diseases, inflammatory conditions, stroke and myocardial infarction (Holdenreider & Stieber, 2009).

Mononucleosomes and oligonucleosomes can be detected by Enzyme-Linked ImmunoSorbant Assay (ELISA) and several methods have been reported (Salgame et al, 1997; Holdenrieder et al, 2001; van Nieuwenhuijze et al, 2003). These assays typically employ an anti-histone antibody (for example anti-H2B, anti-H3 or anti-H1, H2A, H2B, H3 and H4) as capture antibody and an anti-DNA or anti-H2A-H2B-DNA complex antibody as detection antibody. Using these assays, workers in the field report that the level of nucleosomes in serum is higher (by up to an order of magnitude) than in plasma samples taken from the same patients. This is also true for serum and plasma measurements of DNA made by PCR (Holdenrieder et al, 2005). The reason for this is not known but the authors speculate that it may be due to additional release of DNA during the clotting process. However, we have found that the results of nucleosome ELISA assays of the current art do not agree with each other. Furthermore, although most circulating DNA in serum or plasma is reported to exist as mono-nucleosomes and oligo-nucleosomes (Holdenrieder et al, 2001), measured levels of nucleosomes and DNA in serum or plasma do not agree well. The correlation coefficient between ELISA results for circulating cell free nucleosomes levels and circulating DNA levels as measured by real time PCR (Polymerase Chain Reaction) has been reported to be r=0.531 in serum and r=0.350 in plasma (Holdenrieder et al, 2005).

Current nucleosome ELISA methods are used in cell culture, primarily as a method to detect apoptosis (Salgame et al, 1997; Holdenrieder et al, 2001; van Nieuwenhuijze et al, 2003), and are also used for the measurement of circulating cell free nucleosomes in serum and plasma (Holdenrieder et al, 2001). Cell free serum and plasma nucleosome levels released into the circulation by dying cells have been measured by ELISA methods in studies of a number of different cancers to evaluate their use as a potential biomarker (Holdenrieder et al, 2001). Mean circulating nucleosome levels are reported to be high in most, but not all, cancers studied. The highest circulating nucleosome levels were observed in lung cancer subjects. The lowest levels were observed in prostate cancer, which were within the normal range of healthy subjects. However, patients with malignant tumours are reported to have serum nucleosome concentrations that varied considerably and some patients with advanced tumour disease were found to have low circulating nucleosome levels, within the range measured for healthy subjects (Holdenrieder et al, 2001). Because of this and the variety of non-cancer causes of raised nucleosome levels, circulating nucleosome levels are not used clinically as a biomarker of cancer (Holdenrieder and Stieber, 2009). Surprisingly we have shown that many cancer subjects whose circulating nucleosome levels are low or undetectable as measured by these nucleosome ELISA methods of the current art, do in fact have raised levels of circulating cell free nucleosomes. We have designed and demonstrated novel ELISA methods for nucleosomes that detect nucleosomes not detected by ELISA methods of the current art.

ELISA methods for the detection of histone PTMs are also known in the art. ELISA methods for PTM detection in free histone proteins (not attached to other histones and DNA in a nucleosome complex) are used for the detection of PTMs in histones extracted, usually by acid extraction, from cell lysates. An immunoassay for the detection of PTMs in circulating cell free nucleosomes has been reported (Bawden et al, 2005). A method for ELISA detection of histone PTMs in purified nucleosomes directly coated to microtitre wells has recently been reported (Dai et al, 2011). In this method, nucleosomes obtained by digestion of chromatin extracts from cultured cells are coated directly to microtitre wells and reacted with anti-PTM antibodies. It will be clear to those skilled in the art that this method requires relatively pure nucleosome samples and is not suitable for the direct measurement of histone PTMs in complex biological media such as blood, plasma or serum.

A modified chromatin immunoprecipitation (ChIP) method for the detection of a histone PTM (H3K9Me, histone H3 monomethylated at lysine residue K9) in cell free nucleosomes associated with a particular DNA sequence has been reported in plasma. The level of sequence specific histone methylation was reported to be independent of the concentration of circulating nucleosomes (Deligezer et al, 2008).

Histone variants (also known as histone isoforms) are known to be epigenetic regulators of gene expression (Herranz and Esteller, 2007). Histone variants have been studied in vivo and in vitro using a variety of techniques including knock-down studies of the gene encoding a particular variant (for example using RNAi knock-down), chromatin immunoprecipitation, stable isotope labeling of amino acids and quantitative mass spectrometry proteomics, immunohistochemistry and Western Blotting (Whittle et al, 2008; Boulard et al, 2010; Sporn et al, 2009; Kapoor et al, 2010; Zee et al, 2010; Hua et al, 2008).

Immunohistochemistry studies of histone variant expression in tissue samples removed at surgery or by biopsy from subjects diagnosed with lung cancer, breast cancer and melanoma have been reported. These immunohistochemistry studies report that staining of histone macroH2A (mH2A) and H2AZ variants in resected cancer tissue samples may have prognostic application in these cancers (Sporn et al, 2009, Hua et al, 2008, Kapoor et al, 2010). One disadvantage of immunohistochemical methods for clinical use is that tissue sample collection is invasive involving surgery or biopsy. Another disadvantage of immunohistochemistry methods is that they are unsuited for early diagnosis or for screening diagnostics as a reasonable expectation of the disease must usually already exist before a biopsy or tissue resection is made. Minimally invasive blood ELISA tests are suitable for a wider range of applications and would overcome these disadvantages and be preferable for the patient as well as faster, lower cost and more high-throughput for the healthcare provider.

However, cell free histone variants in cell free nucleosomes have not been measured in blood or other media. No studies on the presence or absence of histone variants in cell free nucleosomes in blood have been reported. There are currently no methods for the detection or measurement of histone variants in intact cell free nucleosomes nor has any such measurement been suggested or contemplated In addition to the epigenetic signaling mediated by nucleosome position and nucleosome structure (in terms of both constituent histone protein variant and PTM structures), control of gene expression in cells is also mediated by modifications to DNA nucleotides including the cytosine methylation status of DNA. It has been known in the art for some time that DNA may be methylated at the 5 position of cytosine nucleotides to form 5-methylcytosine. Methylated DNA in the form of 5-methylcytosine is reported to occur at positions in the DNA sequence where a cytosine nucleotide occurs next to a guanine nucleotide. These positions are termed "CpG" for shorthand. It is reported that more than 70% of CpG positions are methylated in vertebrates (Pennings et al, 2005). Regions of the genome that contain a high proportion of CpG sites are often termed "CpG islands", and approximately 60% of human gene promoter sequences are associated with such CpG islands (Rodriguez-Paredes and Esteller, 2011). In active genes these CpG islands are generally hypomethylated. Methylation of gene promoter sequences is associated with stable gene inactivation. DNA methylation also commonly occurs in repetitive elements including Alu repetitive elements and long interspersed nucleotide elements (Herranz and Esteliar, 2007; Allen et al, 2004).

The involvement of DNA methylation in cancer was reported as early as 1983 (Feinberg and Vogelstein, 1983). DNA methylation patterns observed in cancer cells differ from those of healthy cells. Repetitive elements, particularly around pericentromeric areas, are reported to be hypomethylated in cancer relative to healthy cells but promoters of specific genes have been reported to be hypermethylated in cancer. The balance of these two effects is reported to result in global DNA hypomethylation in cancer cells (Rodriguez-Paredes; Esteller, 2007).

Hypermethylation of certain specific genes can be used as a diagnostic biomarker for cancers. For example a method reported for detection of hypermethylation of the Septin 9 gene by PCR amplification of DNA extracted from plasma was reported to detect 72% of colon cancers with a false positive rate of 10% (Grutzmann et al, 2008). The DNA methylation status of specific genes or loci is usually detected by selective bisulphite deamination of cytosine, but not 5-methylcytosine, to uracil, leading to a primary DNA sequence change that can be detected by sequencing or other means (Allen et al, 2004).

Global DNA hypomethylation is a hallmark of cancer cells (Estellar 2007 and Hervouet et al, 2010). Global DNA methylation can be studied in cells using immunohistochemistry (IHC) techniques. Alternatively the DNA is extracted from the cells for analysis. A number of methods have been reported for the detection of global methylation in DNA extracted from cells or other media including restriction digestion and nearest-neighbour analysis, fluorescent assays using chloracetaldehyde, inverse determination by methylation of all CpG sites using DNA methyltransferase in conjunction with tritium-labeled S-adenosyl methionine to calculate the amount of unmethylated CpG and digestion of DNA into single nucleotides for analysis by high-performance liquid chromatography, thin-layer chromatography, or liquid chromatography followed by mass spectroscopy. The disadvantages of these methods are that they are labour intensive and/or require large amounts of good quality extracted DNA (Allen et al 2004). PCR based methods involving bisulfite deamination overcome the need for large amounts of DNA but must amplify specific genome regions, typically repetitive sequences, as indicative of the total genome content of 5-methylcytosine (Allen et al 2004). These methods for global DNA methylation measurement have been used to study DNA extracted from a variety of cells and tissues. Some workers have studied DNA extracted from white blood cells in whole blood as this is easier to obtain in a minimally-invasive manner (Moore et al, 2008; Ting Hsiung et al, 2007; Mansour et al, 2010). Liquid Chromatography with mass spectrometry is considered the gold standard for global DNA methylation measurement but it is costly, and the DNA must be digested to the single nucleotide level prior to analysis (Vasser et al, 2009).

Recent methods for the estimation of global DNA methylation include ultra high-pressure liquid chromatography with mass spectrometry of hydrolysed DNA extracted from tissue (Zhang et al, 2011) and a methylation-specific digital sequencing (MSDS) method (Ogoshi et al 2011). A classical competitive immunoassay for global DNA methylation (as well as a similar assay for global 5-hydroxymethylcytosine methylation) has been described. In this method DNA extracted from cells or tissues is added to a microtitre well coated with a 5-methylated cytidine conjugate, an anti-5-methylcytidine antibody is added and the distribution of antibody binding between the coated 5-methylcytidine conjugate and the methylated DNA in the extracted sample is compared to that of known standards to estimate the global DNA methylation level present in the sample (Cell Biolabs, 2011). In another immunoassay like method, DNA extracted from tissues or from plasma or serum samples is coated to a microtitre well and methylated DNA is detected using an anti-5-methylcytosine antibody (Vasser, et al, 2009; Epigentek, 2009). A disadvantage of these methods is that they require extraction of DNA involving the denaturation and removal of all nucleosome and chromatin structure from the DNA. They thus cannot measure nucleosome bound nucleotides and are not suited for example; for the direct measurement of global DNA methylation in biological fluids such as tissue lysate, blood, plasma or serum without a DNA extraction step.

5-hydroxymethyl modification of cytosine bases in DNA has also been reported. The role of 5-hydroxymethylation is not yet well understood but it appears to be involved in gene regulation (Stroud et al, 2011).

Current methods for the detection of global DNA methylation involve extraction or purification of the DNA and are not suitable for rapid, high throughput, low cost, minimally-invasive diagnostic methods. Similarly, analysis of DNA for other modified or unusual bases (for example uracil, inosine, xanthine, hypoxanthine) can only be investigated by the analysis of substantially pure or extracted DNA. Such analysis cannot be carried out directly in complex biological media such as tissue lysate, blood, plasma or serum.

Cell free nucleosomes containing 5-methylcytosine or any other particular nucleotides or modified nucleotides have not been measured in blood or any other media. No studies on the presence or absence of cell free nucleosomes containing particular nucleotides in blood have been reported. Assays for cell free nucleosomes containing particular nucleotides have not been suggested or contemplated.

There are currently no methods for the detection or measurement of cell free nucleosome associated nucleotides.

We now report simple immunoassay methods for the direct estimation of the nucleosome associated nucleotides including for example, 5-methylcytosine and 5-hydroxymethylcytosine, in biological samples without extraction. Surprisingly we have shown that nucleosome associated nucleotides can be detected in blood samples in which nucleosomes are not detected by ELISA methods of the current art.

SUMMARY OF THE INVENTION

According to a first aspect of the invention there is provided a cell free nucleosome comprising a DNA base, nucleotide or nucleoside for use as a biomarker for the diagnosis of cancer, cardiomyopathy, systemic lupus erythematosus, colitis, chronic obstructive pulmonary disorder, Crohn's disease and rheumatoid arthritis.

According to a second aspect of the invention there is provided a method for detecting the presence of a nucleosome containing a DNA base, nucleotide or nucleoside in a sample which comprises the steps of:
  (i) contacting the sample with a binding agent which binds to the DNA base, nucleotide or nucleoside;
  (ii) detecting or quantifying the binding of said binding agent to the DNA base, nucleotide or nucleoside in the sample; and
  (iii) using the presence or degree of such binding as a measure of the presence of nucleosomes containing the DNA base, nucleotide or nucleoside in the sample.

According to a third aspect of the invention there is provided a method for detecting the presence of a nucleosome containing a DNA base, nucleotide or nucleoside in a sample which comprises the steps of:
  (i) contacting the sample with a first binding agent which binds to nucleosomes;
  (ii) contacting the nucleosomes or sample with a second binding agent which binds to the DNA base, nucleotide or nucleoside;
  (iii) detecting or quantifying the binding of said second binding agent to the DNA base, nucleotide or nucleoside in the sample; and
  (iv) using the presence or degree of such binding as a measure of the presence of nucleosomes containing the DNA base, nucleotide or nucleoside in the sample.

According to a fourth aspect of the invention there is provided a method for detecting the presence of a nucleosome containing a DNA base, nucleotide or nucleoside in a sample which comprises the steps of:
  (i) contacting the sample with a first binding agent which binds to the DNA base, nucleotide or nucleoside;
  (ii) contacting the nucleosomes or sample with a second binding agent which binds to nucleosomes;
  (iii) detecting or quantifying the binding of said second binding agent to nucleosomes in the sample; and
  (iv) using the presence or degree of such binding as a measure of the presence of nucleosomes containing the DNA base, nucleotide or nucleoside in the sample.

According to a further aspect of the invention there is provided a method for detecting the presence of a nucleosome containing a DNA base, nucleotide or nucleoside in a cell which comprises the steps of:
  (i) isolating chromatin from a cell;
  (ii) digesting, sonicating or otherwise breaking down the chromatin to form mono-nucleosomes and/or oligo-nucleosomes; and (iii) detecting or measuring the presence of the DNA base, nucleotide or nucleoside in the said nucleosomes according to a method of the invention.

According to a further aspect of the invention there is provided a method for detecting or diagnosing a disease status in an animal or a human subject which comprises the steps of:
(i) detecting or measuring nucleosomes containing a DNA base, nucleotide or nucleoside in a body fluid of a subject; and
(ii) using the nucleosome associated DNA base, nucleotide or nucleoside level detected to identify the disease status of the subject.

According to a further aspect of the invention there is provided a method for assessment of an animal or a human subject for suitability for a medical treatment which comprises the steps of:
(i) detecting or measuring nucleosomes containing a DNA base, nucleotide or nucleoside in a body fluid of the subject; and
(ii) using the nucleosome associated DNA base, nucleotide or nucleoside level detected as a parameter for selection of a suitable treatment for the subject.

According to a further aspect of the invention there is provided a method for monitoring a treatment of an animal or a human subject which comprises the steps of:
(i) detecting or measuring nucleosomes containing a DNA base, nucleotide or nucleoside in a body fluid of the subject;
(ii) repeating the detection or measurement of nucleosomes containing a DNA base, nucleotide or nucleoside in a body fluid of the subject on one or more occasions; and
(iii) using any changes in the nucleosome associated DNA base, nucleotide or nucleoside level detected as a parameter for any changes in the condition of the subject.

According to a further aspect of the invention there is provided a method for identifying a DNA base, nucleotide or nucleoside biomarker for detecting or diagnosing a disease status in an animal or a human subject which comprises the steps of:
(i) detecting or measuring nucleosomes containing the DNA base, nucleotide or nucleoside in a body fluid of the subject;
(ii) detecting or measuring nucleosomes containing the DNA base, nucleotide or nucleoside in a body fluid of a healthy subject or a control subject; and
(iii) using the difference between the levels detected in diseased and control subjects to identify whether a DNA base, nucleotide or nucleoside is useful as a biomarker for the disease status.

According to a further aspect of the invention there is provided a biomarker identified by said method of the invention.

According to a further aspect of the invention there is provided a kit for the detection of a nucleosome associated DNA base, nucleotide or nucleoside which comprises a ligand or binder specific for the DNA base, nucleotide or nucleoside or component part thereof, or a structural/shape mimic of the DNA base, nucleotide or nucleoside or component part thereof, together with instructions for use of the kit.

BRIEF DESCRIPTION OF THE FIGURES

FIG. 19. Cell free nucleosome associated 5-methylcytosine levels detected for EDTA plasma samples taken from lung and colon cancer patients with increasing tumour size, stage and nodal development of disease.

DETAILED DESCRIPTION OF THE INVENTION

According to a first aspect of the invention there is provided a cell free nucleosome comprising a DNA base, nucleotide or nucleoside for use as a biomarker for the diagnosis of cancer, cardiomyopathy, systemic lupus erythematosus, colitis, chronic obstructive pulmonary disorder, Crohn's disease and rheumatoid arthritis.

In one embodiment, the nucleosome is a mononucleosome or oligonucleosome.

According to one particular aspect of the invention which may be mentioned, there is provided the use of a DNA base, nucleotide or nucleoside as a biomarker for the diagnosis of cancer.

In one embodiment, the cancer is a cancer of the bladder, breast, colon, cervix, esophagus, kidney, large intestine, lung, oral cavity, ovary, pancreas, prostate, rectum, skin or stomach. In one particular embodiment which may be mentioned, the cancer is a cancer of the colon, lung, oral cavity or pancreas.

We have developed ELISA tests for the detection and measurement of nucleosomes containing the DNA bases 5-methylcytosine and 5-hydroxymethylcytosine. We have used an anti-histone antibody as capture antibody for these assays in combination with an appropriate specific anti-nucleotide antibody. We have used the assays to show that nucleosomes containing specific nucleotides can be measured in blood samples taken from subjects with cancer and are discriminating for use as non-invasive or minimally invasive biomarkers. The nucleosome associated DNA 5-methylcytosine levels, relative to levels of other nucleosome epitopes, detected in serum and plasma samples taken from diseased subjects differed from those detected in samples from healthy subjects. In addition the pattern of levels of the nucleotides detected in nucleosomes in samples taken from subjects with different diseases was found to differ such that a differential diagnosis of disease was possible, particularly when the nucleosome associated nucleotide patterns were examined in combination with the patterns determined for nucleosomes containing different histone variants and histone modifications. It will be clear to those skilled in the art that inclusion of tests for nucleosomes containing different or additional nucleotides would be likely to improve the discrimination of differential diagnosis using such patterns.

Figure 3:
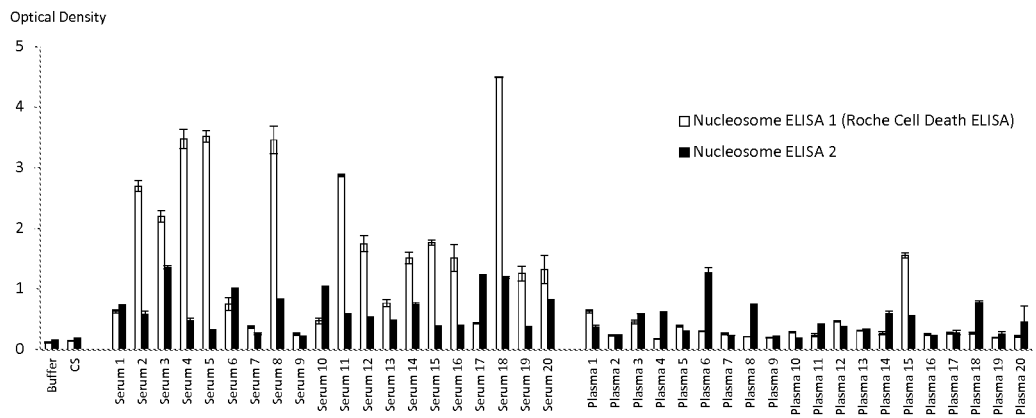
FIG. 3. Nucleosome levels detected for serum and EDTA plasma samples taken from 20 healthy volunteers using nucleosome ELISA methods of the current art.
Figure 4:
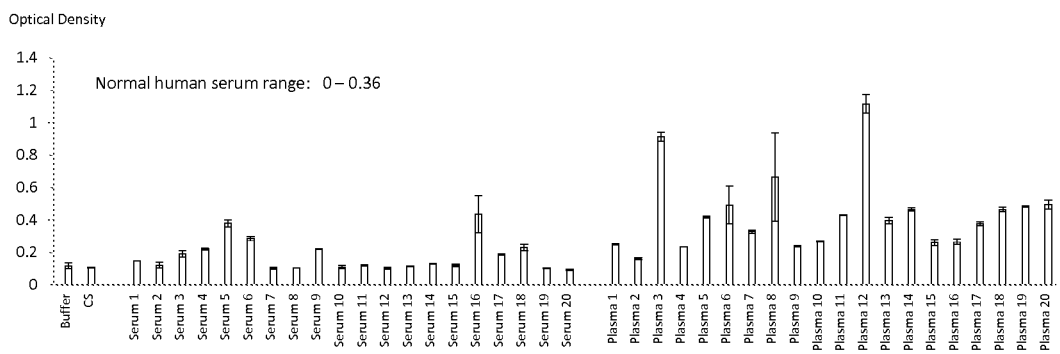
FIG. 4. Cell-free nucleosome associated levels of histone variant mH2A1.1 detected for serum and EDTA plasma samples taken from 20 healthy volunteers.
Figure 5:
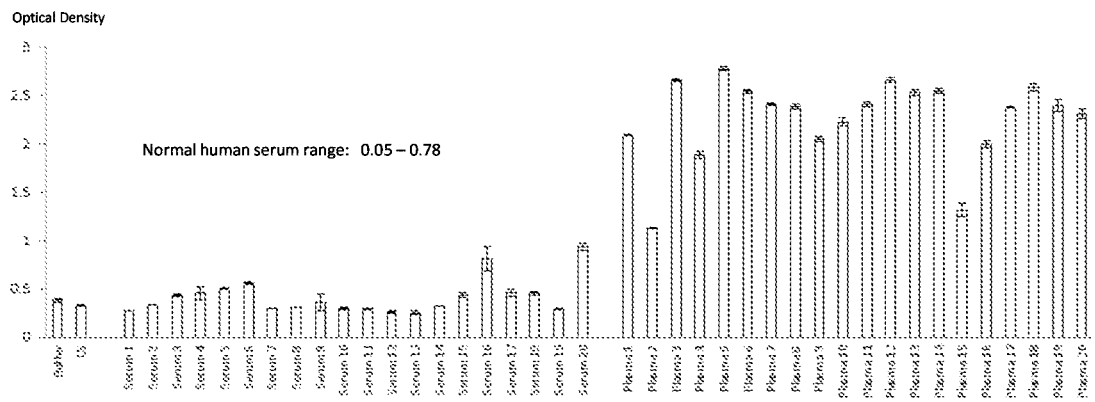
FIG. 5. Cell-free nucleosome associated levels of histone variant mH2A2 detected for serum and EDTA plasma samples taken from 20 healthy volunteers.
Figure 6:
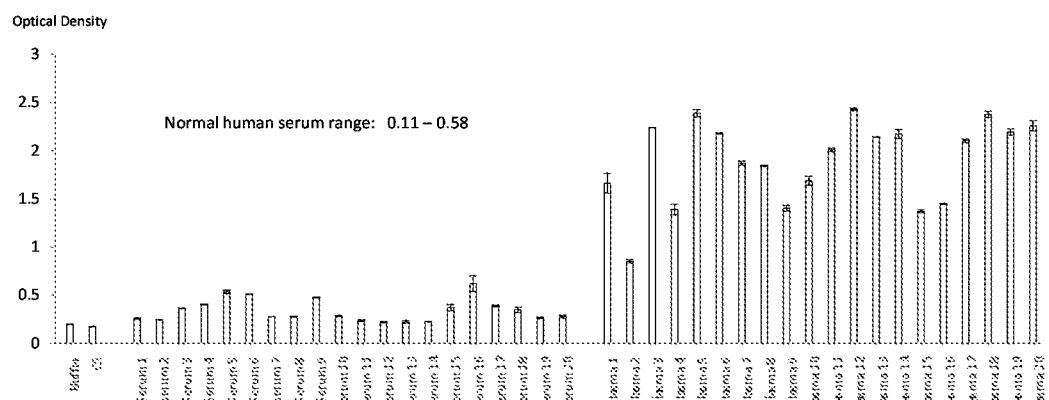
FIG. 6. Cell-free nucleosome associated levels of histone variant H2AZ detected for serum and EDTA plasma samples taken from 20 healthy volunteers.
Figure 7:
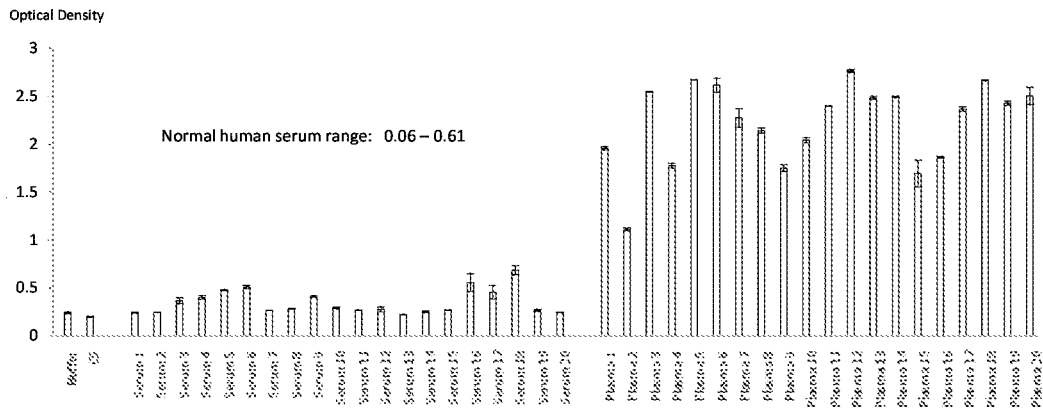
FIG. 7. Cell-free nucleosome associated levels of histone modification P-H2AX(Ser139) detected for serum and EDTA plasma samples taken from 20 healthy volunteers.

To investigate levels of nucleosomes found in healthy subjects using the methods of the current art we measured nucleosomes in serum and plasma samples, taken from the 20 healthy subjects. Both methods of the current art produced higher signals in serum samples taken from healthy subjects than in plasma samples. The results are shown in FIG. 3. This is consistent with published data that nucleosome levels are higher in serum than plasma (*Holdenrieder et al, 2001).

Figure 8:
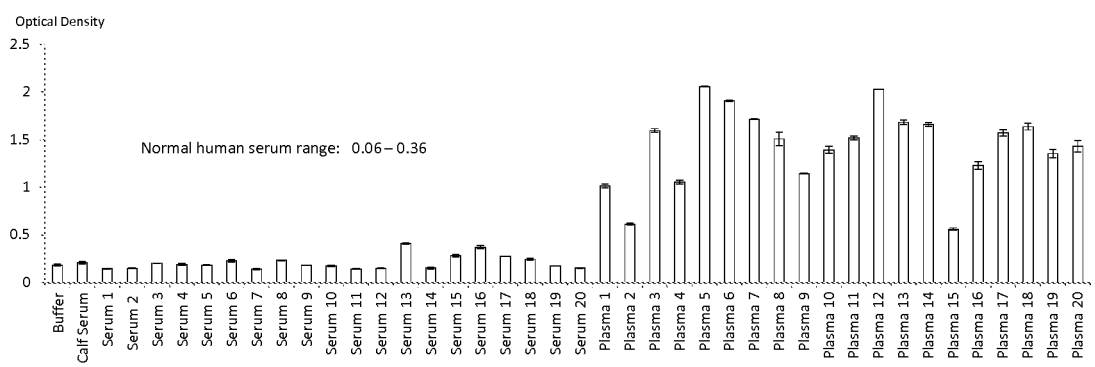
FIG. 8. Cell-free nucleosome associated levels of 5-methylcytosine methylated DNA detected for serum and EDTA plasma samples taken from 20 healthy volunteers using the ELISA of the invention.
Figure 9:
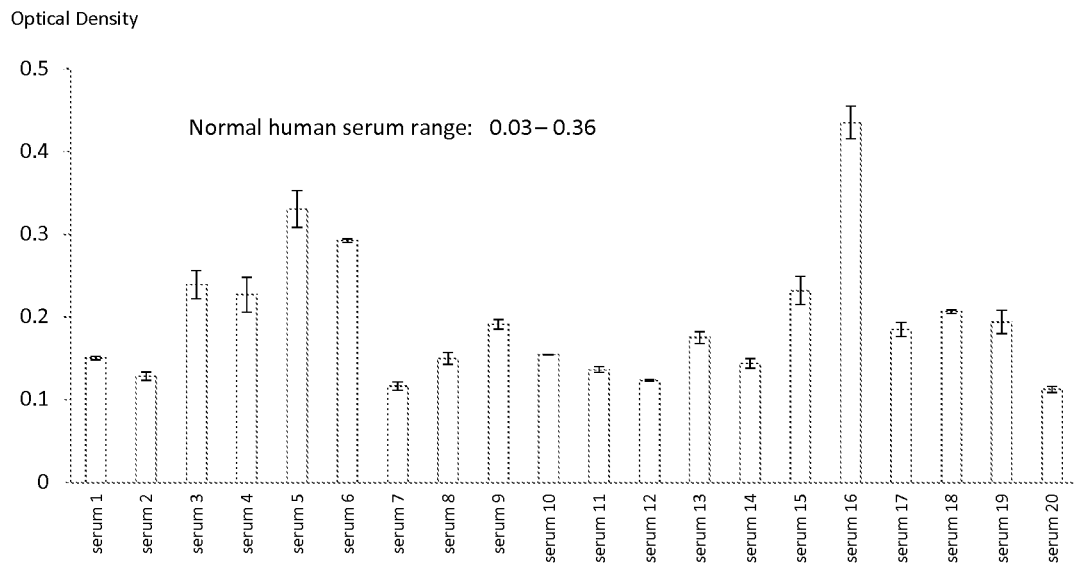
FIG. 9. Cell-free nucleosome associated levels of 5-hydroxymethylcytosine methylated DNA detected for serum samples taken from 20 healthy volunteers using the ELISA of the invention.
Figure 10:
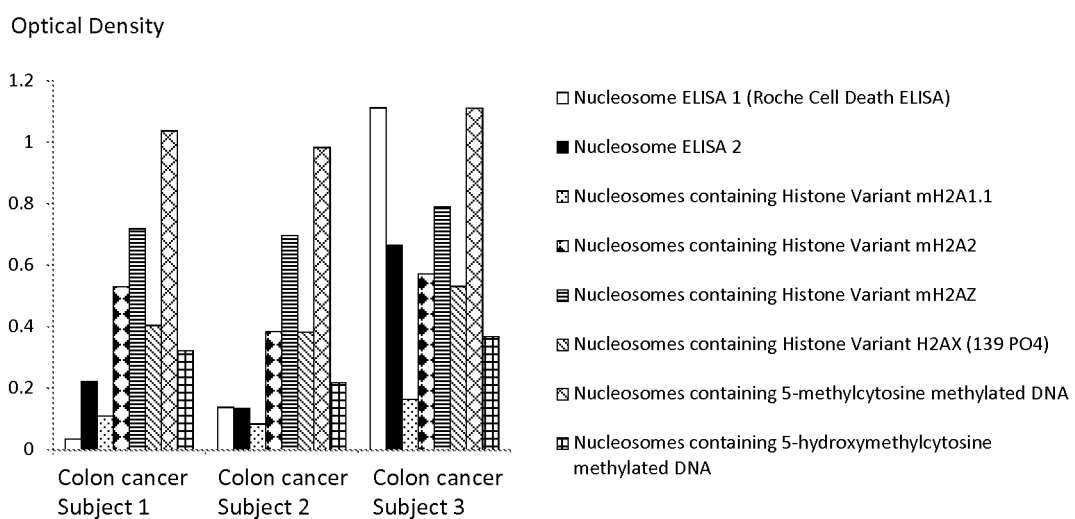
FIG. 10. Cell-free nucleosome associated levels of nucleotides and types of histones detected for EDTA plasma samples taken from 3 colon cancer subjects.
Figure 11:
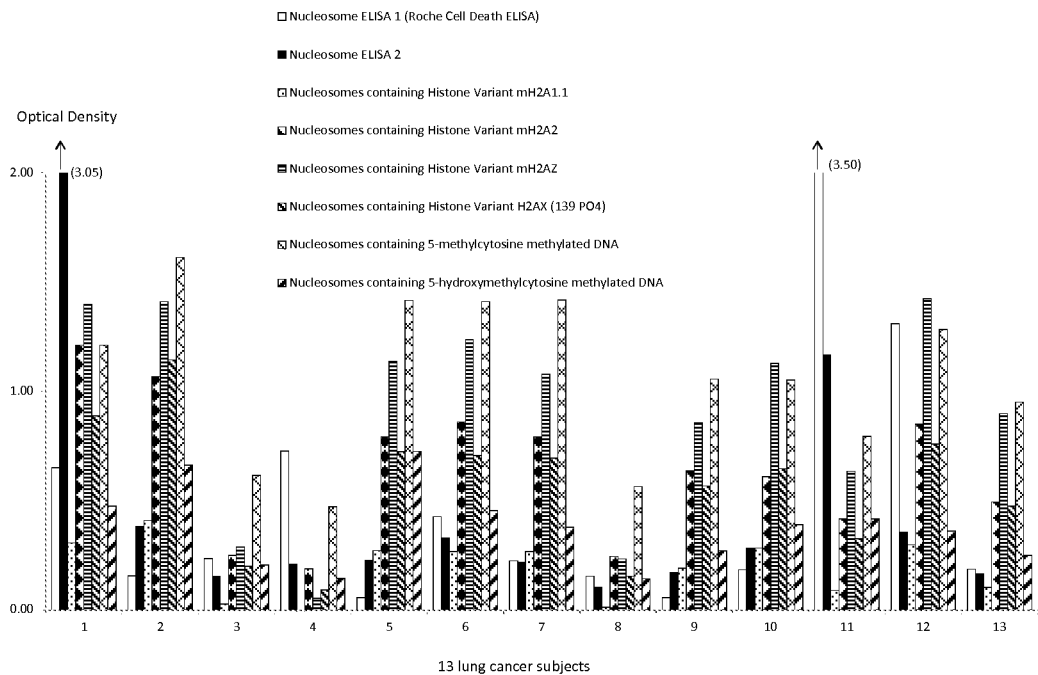
FIG. 11. Cell-free nucleosome associated levels of nucleotides and types of histones detected for EDTA plasma samples taken from 13 lung cancer subjects.
Figure 12:
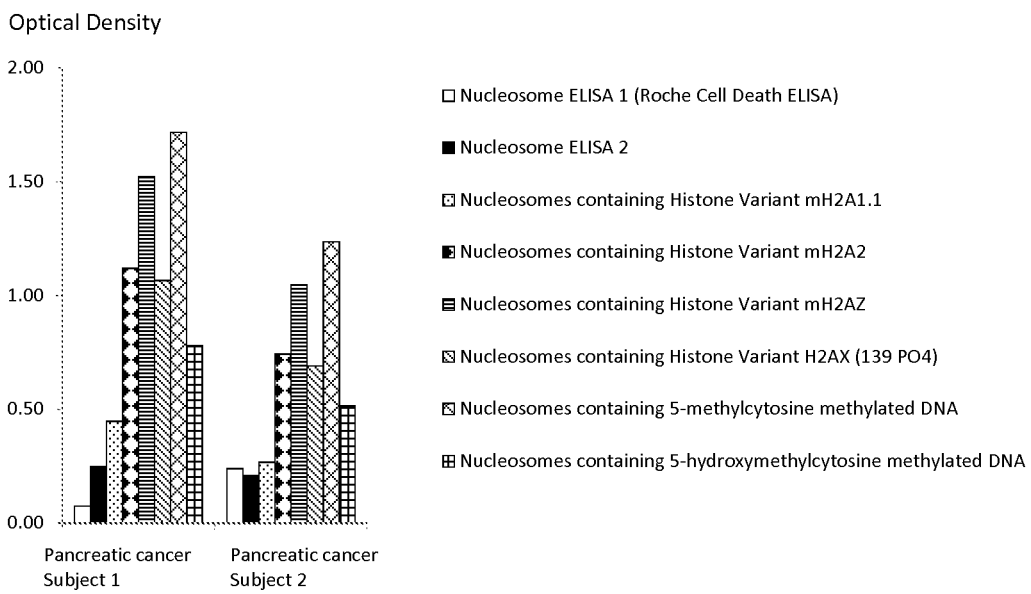
FIG. 12. Cell-free nucleosome associated levels of nucleotides and types of histones detected for EDTA plasma samples taken from 2 pancreatic cancer subjects.
Figure 13:
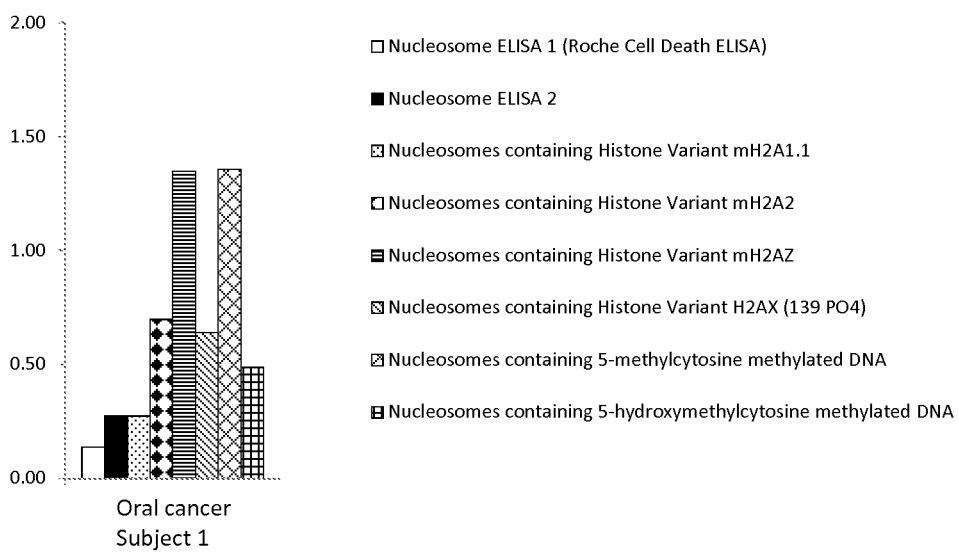
FIG. 13. Cell-free nucleosome associated levels of nucleotides and types of histones detected for EDTA plasma samples taken from 1 oral cancer subject.

To investigate levels of nucleosomes found in healthy subjects using the methods of the invention we measured nucleosomes containing the modified nucleotide 5-methylcytosine in the sera of 20 healthy subjects and in healthy bovine serum. The serum results were low or undetectable for all 20 healthy subjects. We also measured nucleosomes containing the modified nucleotide 5-methylcytosine in EDTA plasma samples, taken from the 20 healthy subjects, and, surprisingly, higher signals were observed. High levels of cell free nucleosomes containing the modified nucleotide 5-methylcytosine were detected by methods of the present invention in healthy human EDTA plasma but lower levels were detected in healthy human serum as shown in FIG. 8. FIGS. 4-9 show that similar results were obtained for other nucleosome structures. This finding is unexpected and different to both the published results (*Holdenrieder et al, 2001) and the results we found for nucleosome ELISA methods of the current art. Thus surprisingly the methods of the invention produce opposite results to methods of the current art for the relative levels of nucleosomes that occur in serum and EDTA plasma samples.

Figure 15:
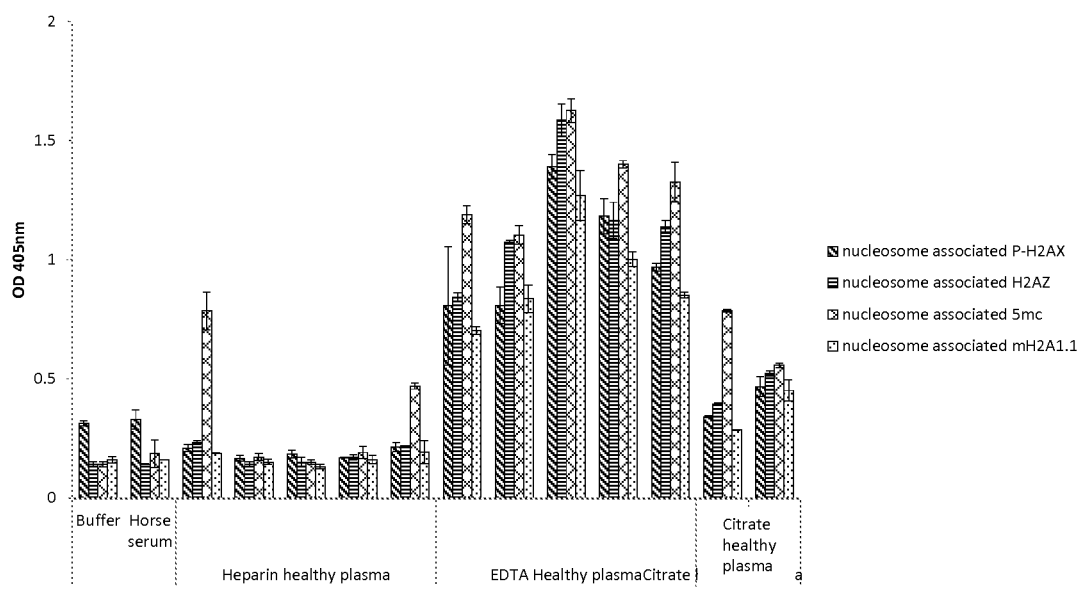
FIG. 15. Cell free nucleosome associated levels of 5-methylcytosine (5 mc), mH2A1.1, H2AZ and P-H2AX (Ser139) detected in EDTA plasma, citrate plasma and heparin plasma samples taken from healthy volunteers using the ELISA method of the invention.

We investigated whether nucleosome structures are detectable in all of the various common types of plasma that can be collected. We found that high levels of cell free nucleosome associated 5-methylcytosine were detectable by the method of the invention in EDTA plasma and, to a lesser extent, in citrate plasma taken from healthy subjects, but that nucleosome associated 5-methylcytosine was low or undetectable over buffer or horse serum background signals in most (3 of 5) heparin plasma samples taken from healthy subjects. The results are shown in FIG. 15. To summarise, cell free nucleosomes are found in relatively high concentrations in most or all EDTA plasma and citrate plasma samples taken from healthy subjects using the method of the invention, but are low or absent in a majority of heparin plasma or serum samples taken from healthy subjects. It is therefore clear that the precise choice of sample type will be critical for different applications.

We have shown that sample selection for the detection of cell free nucleosomes containing particular nucleotide structures involves several parameters. These include the low levels of cell free nucleosomes generally present in serum and heparin plasma samples taken from healthy subjects, the higher levels generally present in EDTA and citrate plasma samples taken from healthy subjects, the recommendation that serum samples containing cell free nucleosomes should be stabilised by the addition of EDTA after separation of the serum from the clot (*Holdenrieder et al, 2001), and the serum sampling protocol. Other stabilizing agents (for example protease inhibitors) may also be used. Where possible we used serum samples centrifuged within 1 hour of venepuncture after which 10 mM EDTA was added and the sample frozen.

Figure 16:
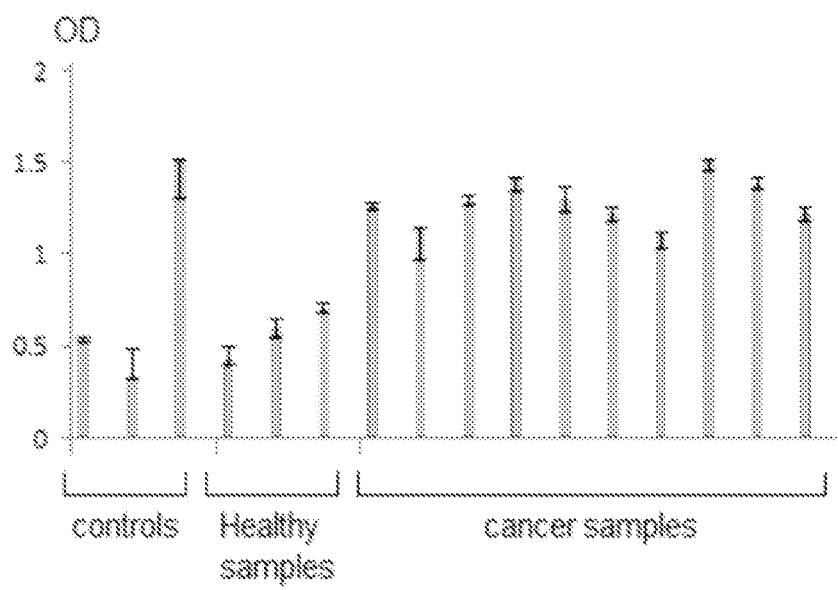
FIG. 16. Cell free nucleosome associated 5-methylcytosine levels detected for serum samples taken from 3 healthy volunteers and 10 colon cancer subjects detected using the ELISA method of the invention.

The choice of blood sample type for clinical samples should be made on the basis of optimal clinical discrimination for the particular test. Following our finding of consistently low nucleosome levels by the method of the invention in the serum of healthy subjects, we measured nucleosomes containing the nucleotide 5-methylcytosine in serum samples taken from subjects with cancer. Clinical sensitivity of up to 100% was observed as shown in FIG. 16 for colon cancer samples.

We also measured the relative levels of cell free nucleosomes containing the nucleotides 5-methylcytosine and 5-hydroxymethylcytosine and other nucleosome structures in EDTA plasma samples taken from subjects with a variety of diseases. The levels of cell free nucleosomes are high in EDTA plasma samples taken from both healthy subjects and diseased subjects and EDTA plasma samples would therefore seem unlikely to be the best sample choice for a sensitive discriminator of diseased and healthy subjects. However, we have shown that the levels and the composition of circulating cell free nucleosomes, in terms of the relative levels of nucleosomes containing different nucleotides (as well as other nucleosome structures), varies between diseased and healthy individuals and also between different diseases. We are thus the first to report both that (i) high levels of circulating nucleosomes are present in all or most EDTA plasma samples taken from both healthy and diseased subjects but this is not true of all blood sample types; and also that (ii) surprisingly, detection of disease and discrimination of disease type can none the less be made by analysis of these EDTA plasma nucleosomes on the basis of the levels and structural profile of one or more of the relative types of nucleosome structures present in the plasma of diseased and healthy subjects.

We measured cell free nucleosomes in EDTA plasma taken from healthy subjects and 117 subjects with a variety of cancer types in two experiments consisting of 55 and 62 cancer subjects respectively. In total 78% (91 of 117) of cancer samples were correctly identified as positive for cancer using the method of the invention for nucleosome associated 5-methylcytosine using a cut-off level of the mean result for healthy subjects +2 standard deviations of the mean.

Figure 17:
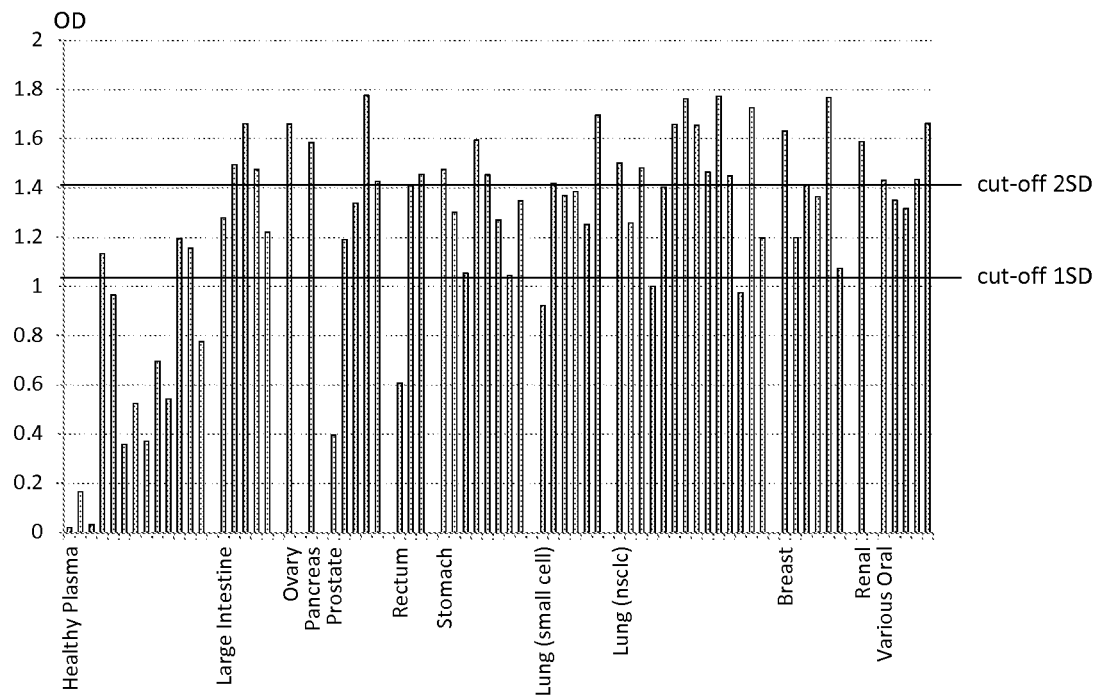
FIG. 17. Cell free nucleosome associated 5-methylcytosine levels detected for EDTA plasma samples taken from 13 healthy volunteers and 55 cancer patients. The cut-off points defined as the mean value of the healthy samples plus one or two standard deviations in the mean are shown.

In the first of these 2 experiments we measured cell free nucleosomes in EDTA plasma taken from 13 healthy subjects and 55 subjects with cancer of the stomach, large intestine, rectum, lung (small cell carcinoma and various non-small cell carcinomas), breast, ovary, pancreas, prostate, kidney and various oral cancers (oral cavity, palate, pharynx and larynx). All of the 13 samples from healthy subjects and cancer patients were positive for nucleosomes. However, the levels detected in samples taken from cancer subjects were higher than found in samples from healthy subjects and the results showed that healthy and cancer subjects can be discriminated. For example the normal range calculated in OD terms as the mean±2 standard deviations of the mean, for nucleosome associated 5-methylcytosine was 0-1.41. Using this cut-off value all 13 healthy samples were negative and 30 of the 55 cancer samples were positive. (an overall clinical sensitivity of 55%) including 38% (3 of 8) of stomach, 60% (3 of 5) of large intestinal, 33% (1 of 3) of rectal, 33% (2 of 6) small cell lung, 64% (9 of 14) of non-small cell lung, 33% (2 of 6) of breast, 100% (1 of 1) of ovarian, 100% (1 of 1) of pancreas, 33% (2 of 6) of prostate, 100% (1 of 1) of kidney and 60% (3 of 5) of oral cancer samples. The results are shown in FIG. 17.

Similarly the normal range for the nucleosome associated H2AZ assay was 0-0.95. Using this cut-off level of 0.95; all 13 healthy subjects were negative for elevated nucleosome H2AZ levels. By contrast a positive result for elevated nucleosome H2AZ levels was found for 84% (46 of 55) of cancer samples (an overall clinical sensitivity of 84%) including 100% (8 of 8) of stomach 100% (5 of 5) of large intestinal, 67% (2 of 3) of rectal, 83% (5 of 6) of small cell lung, 79% (11 of 14) of non-small cell lung, 50% (3 of 6) breast, 100% (1 of 1) of ovarian, 100% (1 of 1) of pancreas, 80% (4 of 5) of prostate, 100% (1 of 1) kidney and 100% (5 of 5) oral cancer samples.

In one embodiment of the invention a control sample is provided and the cut-off level for the assay to distinguish between positive or negative results is defined in relation to the result for the control sample. This could be any proportion equal to or above or below the level of the control sample result. Patient results below this level are considered negative and patient results above this level are considered positive. There may also be a "grey area" range of patient results very close to the cut-off level for which the decision is considered indeterminate and/or the test should be repeated.

Similarly for the nucleosome associated mH2A1.1 assay the normal range was 0-0.91. Using this cut-off value all 13 healthy samples were negative and 64% (35 of 55) of cancer samples were positive. For the nucleosome associated P-H2AX(Ser139) assay the normal range was 0-1.08. Using this cut-off value all 13 healthy samples were negative and 60% (33 of 55) of cancer samples were positive. Thus some nucleosome assays exhibit better clinical sensitivity than others.

In addition, it is possible to use the pattern of nucleosome structures to improve the clinical utility of the invention. This may be done, for example, by lowering the cut-off point of the nucleosome associated 5-methylcytosine assay to mean+1 standard deviation which gives a range of up to 1.01. In this case the number of false negatives is reduced to 4 giving an improved clinical sensitivity of 93% (51 of 55) at the expense of an increase in false positive results for samples taken from healthy subjects from 0% to 23% (3 of 13). The results are shown in FIG. 17.

Figure 20:
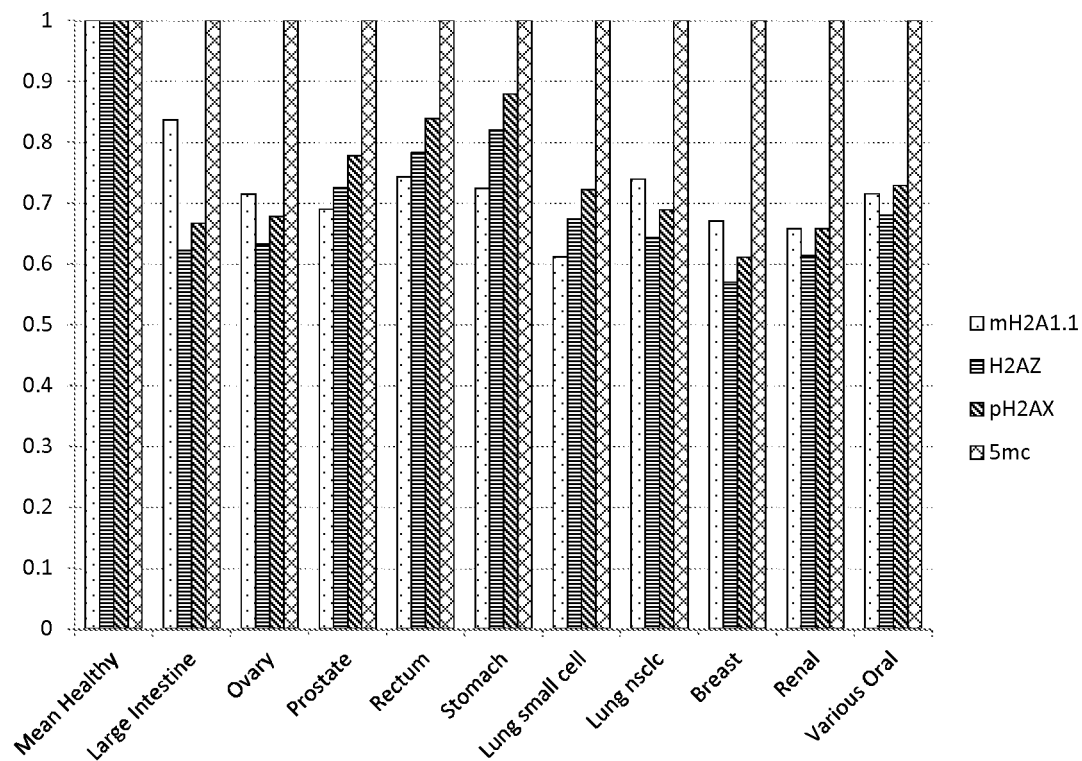
FIG. 20. Mean cell-free nucleosome associated levels of nucleotides and types of histones detected using ELISA methods of the invention for EDTA plasma samples taken from 10 different cancer diseases normalised as a proportion of nucleosome associated 5-methylcytosine (5 mc) methylated DNA levels and expressed relative to the mean proportions found in 11 healthy subjects.
Figure 21:
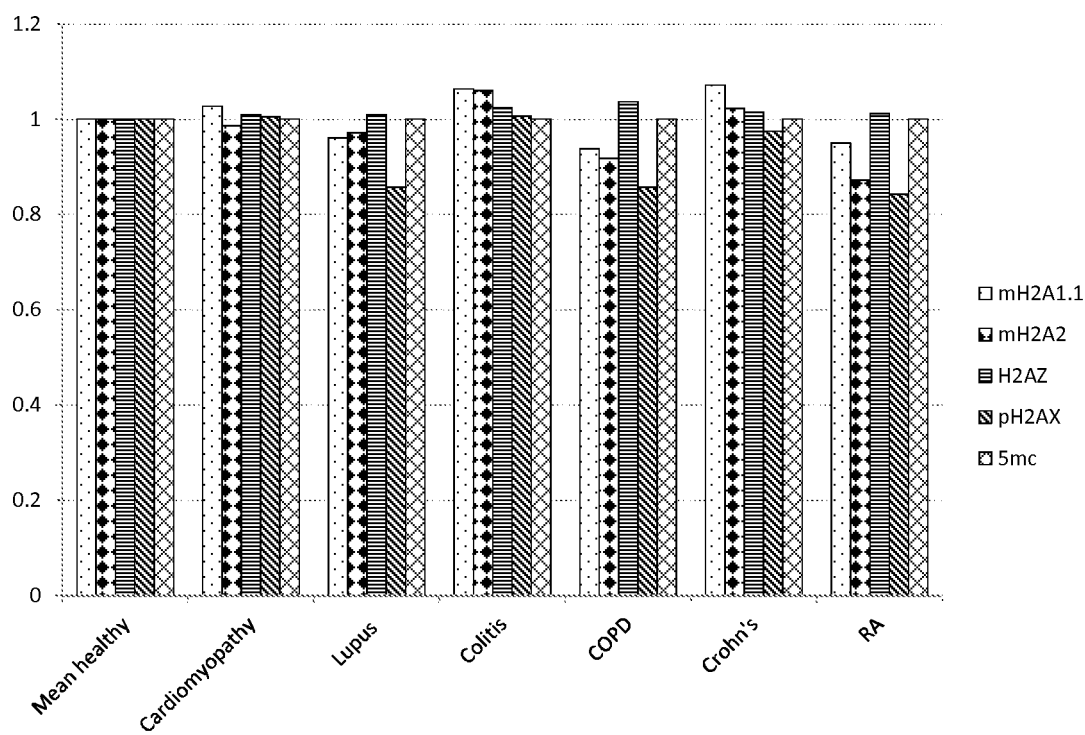
FIG. 21. Mean cell-free nucleosome associated levels of nucleotides and types of histones detected using ELISA methods of the invention for EDTA plasma samples taken from 2 cardiomyopathy patients, 10 systemic lupus erythematosus (lupus) patients, 12 ulcerative colitis patients, 10 chronic obstructive pulmonary disease (COPD) patients, 8 Crohn's disease patients and 10 rheumatoid arthritis (RA) patients normalised as a proportion of nucleosome associated 5-methylcytosine (5 mc) methylated DNA levels and expressed relative to the mean proportions found in 11 healthy subjects.

Samples found positive for 5-methylcytosine associated nucleosomes, or any nucleosomes, can be interrogated for nucleosome structure profile. The nucleosome profile can be used to distinguish between healthy and diseased patients as illustrated in FIGS. 20 and 21 where the relative proportions of various nucleosome structures in diseased patients are expressed relative to those found in healthy patients and patients with other non-cancer diseases. This shows that investigation of multiple nucleosome structures in a test panel can facilitate better clinical discrimination.

Similarly the diagnostic specificity and/or sensitivity of the invention may by increased by combining data from more than one test in the form of ratios. For example use of the nucleosome associated P-H2AX:5-methylcytosine ratio increases the detection of true positive cancer cases from 55% (30 of 55) for nucleosome associated 5-methylcytosine alone, to 67% (37 of 55) at the 2 standard deviation cut-off level whilst maintaining 100% (13 of 13) of negative results for samples taken from healthy subjects.

We measured the levels of circulating cell free nucleosomes containing two different nucleotides in EDTA plasma samples taken from 3 patients with colon cancer, 13 patients with lung cancer, 2 patients with pancreatic cancer and 1 patient with oral cancer and compared these with the levels present in blood samples from 20 healthy subjects as well as with an artificially produced preparation of serum nucleosomes from healthy subjects prepared as described in the literature (*Holdenreider et al, 2001). We have also expressed the levels observed in a normalised form as ratios of the level of nucleosomes containing one particular nucleotide and shown that such ratios or patterns of ratios are useful for the diagnosis both of cancer in general and for the differential diagnosis of specific cancer types. We also investigated whether the level of nucleosome associated 5-methylcytosine varies with disease progression. We observed that the mean level of cell free nucleosomes containing 5-methylcytosine increases with severity of disease and rises with increasing spread of disease to lymph nodes. This provides evidence that the nucleosomes detected are tumour associated.

We also measured the nucleosomes present in these 19 cancer samples using two nucleosome ELISA methods of the current art. Of the 19 cancer subjects studied most were found to have low EDTA plasma nucleosome levels as determined by nucleosome ELISA 1 and 2 of the current art. This result illustrates one reason why the assays of the current art are not used for routine clinical purposes.

We used ELISA methods of the present invention to measure nucleosomes containing 5-methylcytosine and 5-hydroxymethylcytosine nucleotides in the same 19 samples. Surprisingly, high levels of nucleosomes containing 5-methylcytosine were detectable in all 19 samples. Thus in one embodiment the invention provides a novel nucleosome ELISA method capable of detecting nucleosomes not detected by nucleosome assays of the current art.

We have also measured the levels of nucleosomes containing 3 different histone variants and a histone PTM in the same 19 samples taken from cancer subjects as well as a sample of nucleosomes generated from healthy subjects by a method described in the literature (*Holdenrieder et al, 2001). We have used these measurements together with the nucleosome associated nucleotide measurements described here, as a panel of the variety of cell free nucleosomes present in biological fluids taken from subjects with 4 different types of cancers and with nucleosomes generated from healthy subjects. Surprisingly, the pattern of nucleosomes found in the 4 types of cancer investigated (lung, colon, pancreatic and oral) were all distinguishable from that found in the nucleosome sample generated from healthy subjects. Furthermore, the different cancer types were also distinguishable from each other based on the pattern of cell free nucleosomes detectable in the blood of subjects. Thus in one embodiment of the invention there is provided a method for detecting or diagnosing the presence, type, recurrence or severity of a disease or assessing optimal drug or other treatment options by testing a sample for a panel of different nucleosome epitopes consisting of two or more measurements of nucleosomes containing different DNA bases or a combination of one or more DNA bases and one or more histone variants and/or one or more histone modifications and/or measurements of nucleosomes per se, or any combination or ratio of any of these, as an indicator of the health or disease status of a subject.

We similarly used ELISA methods of the invention to detect variability in the nucleotide and histone structures of circulating cell free nucleosomes in a variety of cancer and non-cancer diseases and compared these to the structure of nucleosomes found in healthy subjects. Nucleosomes were found to be present in all the cancer and non-cancer diseases investigated and were found to have profiles that differed from those of healthy subjects.

We studied EDTA plasma samples taken from 2 cardiomyopathy patients, 10 systemic lupus erythematosus (lupus) patients, 12 ulcerative colitis patients, 10 chronic obstructive pulmonary disease (COPD) patients, 8 Crohn's disease patients and 10 rheumatoid arthritis (RA) patients and normalised the levels of various nucleosome structures detected as a proportion of the mean nucleosome associated 5-methylcytosine levels and expressed the results relative to those found in 11 healthy subjects. We found that the diseases were associated with nucleosome structure profiles that differed from those of healthy or cancer subjects. Thus nucleosome structure profiles can be used as a diagnostic tool for the detection, prognosis prediction, monitoring and therapeutic efficacy prediction in a wide variety of non-cancer diseases. The results are shown in FIG. 21.

We also studied the variability in structure of cell-free nucleosomes in terms of nucleotides and types of histones detected using ELISA methods of the invention for EDTA plasma samples taken from 55 patients with 10 different cancer diseases. The levels of various nucleosome structures detected were normalised as a proportion of nucleosome associated 5-methylcytosine (5 mc) methylated DNA levels and expressed relative to the mean proportions found in 11 healthy subjects. We found nucleosomes present in all subjects and nucleosome structure profiles that varied between cancer diseases, non-cancer diseases and healthy subjects. Thus nucleosome structure profiles can be used as a diagnostic tool for the detection, prognosis prediction, monitoring and therapeutic efficacy prediction in cancer and other diseases. The results are shown in FIGS. 20 and 21.

As most circulating DNA in serum or plasma is reported to exist as mono-nucleosomes and oligo-nucleosomes (Holdenrieder et al, 2001), it will be clear to those skilled in the art that methods of the current invention can also be employed to detect or measure cell free methylated DNA per se (as nucleosome associated DNA containing for example; 5-methylcytosine or 5-hydroxymethylcytosine) directly in biological fluids including blood, serum and plasma. The methods of the invention thus employed have advantages of simplicity and speed over methods for measuring methylated DNA of the current art, particularly as extraction of DNA is not involved or required.

It will further be clear that the method of the present invention can be used to detect or measure any nucleic acid or DNA base or nucleic acid analogue or derivative in nucleosomes. Such bases include, without limitation adenine, thymine, guanine, cytosine, uracil, inosine, xanthine, hypoxanthine, 7,8-dihydro-8-oxo-guanine and any derivatives or analogues of these. It will be clear to those skilled in the art that a common nucleotide (for example without limitation; guanine, cytosine, thymine or adenine), will occur in all or most nucleosomes and that the method of the invention using an antibody to a common nucleotide will provide a method to bind and detect virtually all nucleosomes in a sample. Thus in one embodiment the invention provides a novel method for the detection of nucleosomes per se in which nucleosomes containing a common nucleotide are measured as a way of ensuring that all or most nucleosomes are detected.

In a further embodiment the invention provides a novel method for the detection of all nucleosome associated DNA in which nucleosomes containing a common nucleotide are measured as a way of ensuring that all or most nucleosome bound DNA is detected. Furthermore, measurement of two or more DNA bases will provide the basis for the measurement of a ratio of the relative DNA content of those DNA bases. We illustrate such ratios for the relative levels of 5-methylcytosine and 5-hydroxymethylcytosine in samples in FIGS. 10-14 Our data show that the relative levels of 5-methylcytosine and 5-hydroxymethylcytosine detectable differs in different types of cancers and may be used to distinguish such cancers. Other similar ratios would also be useful in the art. For example; by using the present invention to measure an appropriate DNA base (or bases) as a metric for total nucleosome bound DNA and determining the relative level of another base (for example; 5-methylcytosine) it will be clear that the method of the invention can be used to detect the proportion of the DNA which comprises any particular base (for example the percentage of DNA which is methylated in a sample). Thus the methods of the present invention provide a simple and rapid method for measurement of the percentage DNA content of any base in a sample. The method can be used quickly and simply in multiple samples, for example blood samples. The methods of the invention can be used to detect and measure DNA bases in nucleosomes in any sample where such nucleosomes occur including, for example, samples obtained by digestion of chromatin extracted from cells. It will be clear to those skilled in the art that the term nucleotide herein is intended to include without limitation purines, pyrimidines or any other nucleic acid bases and similar molecules with or without associated sugars and with or without phosphorylation and including any analogues, derivatives or mimics of these.

We conclude that the method of the present invention is a successful method for the detection and measurement of nucleosome associated DNA containing particular nucleotides, that this method can also be used successfully as a method for the detection of nucleosomes per se and that it is a superior method for the detection of nucleosomes per se than the methods of the current art and that this method can also be used successfully as a method for the direct detection of cell free DNA per se and for the nucleotide composition of cell free DNA per se and that it is a superior method for the detection of nucleosome associated DNA and its nucleotide composition than the methods of the current art. The method is rapid, low cost and suitable for use in complex biological media and fluids. We have demonstrated that the method of the current invention can be used to detect nucleosomes and nucleosomes containing methylated DNA in blood, and that this may be used as a biomarker for cancer. It will be clear to those skilled in the art that a biomarker present in the blood samples taken from cancer patients has value for a broad range of diagnostic and disease screening purposes for cancer and other diseases which are associated with elevated circulating nucleosomes (Holdenrieder et al, 2001).

To confirm that elevated levels of nucleosomes are not found in healthy subjects using the methods of the invention we measured nucleosomes containing the nucleotides 5-methylcytosine and 5-hydroxymethylcytosine in the sera of 20 healthy subjects and in healthy bovine serum. The serum circulating nucleosome results for both ELISA tests of the invention were low or undetectable for all 20 healthy subjects. We also conducted a similar test in plasma samples, taken from the same 20 healthy subjects and surprisingly, higher signals were observed. This finding is unexpected and quite different from the results we found for nucleosome ELISA methods of the current art.

The invention has been tested on many cancer and non-cancer diseases and has been found effective in the detection of all the diseases tested. This includes the detection of prostate cancer cases which is not detectable by the nucleosome ELISA tests of the current art (Holdenrieder, 2001). It is clear that the invention is effective for the detection of all or most cancers. It will be clear to those skilled in the art that the clinical performance of the invention may be improved further by inclusion of further nucleosome structure tests and by examination of the ratios of different nucleosome structures present.

According to one aspect of the invention there is provided a double antibody, immunometric or sandwich immunoassay method for detecting and measuring cell free nucleosomes containing nucleotides in a sample. One embodiment of this aspect is an immunoassay which comprises the steps of:
  (i) contacting the sample which may contain nucleosomes with a first antibody or other binder which binds to nucleosomes;
  (ii) contacting the nucleosomes or sample with a second antibody or other binder which binds to a nucleotide;
  (iii) detecting and/or quantifying the binding of said second antibody or other binder to a nucleotide in the sample; and
  (iv) using the presence or degree of such binding as a measure of the presence of a nucleosome associated nucleotide in the sample.

According to a second embodiment there is provided a method for detecting and measuring cell free nucleosomes containing nucleotides in a sample by an immunometric immunoassay which comprises the steps of:
  (i) contacting the sample which may contain nucleosomes with a first antibody or other binder which binds to a nucleotide;
  (ii) contacting the nucleosomes or sample with a second antibody or other binder which binds to nucleosomes;
  (iii) detecting and/or quantifying the binding of said second antibody or other binder to nucleosomes in the sample; and
  (iv) using the presence or degree of such binding as a measure of the presence of a nucleosome associated nucleotide in the sample.

A variety of antibodies or other binders may be employed in the invention as a binder which binds to nucleosomes. These include binders directed to bind to epitopes that occur in intact nucleosomes and not in free histones (for example; an epitope found at the junction between two histones in a nucleosome) and also binders directed to any nucleosome component including common nucleosome protein, histone or nucleic acid epitopes.

It will be clear to those skilled in the art that the methods of the invention described include a variety of embodiments including biosensor type assays and label-free assays of the type marketed for example by ForteBio Incorporated of USA. Immunometric immunoassays employ an antibody (or other binder) to bind the analyte. The analyte thus bound is detected as a direct measure of its level or concentration in the original test sample. In contrast "competitive" immunoassays often use a much smaller amount of antibody (or other binder) to bind a proportion of the analyte and a labelled analyte (or analyte analogue) preparation is employed to distribute between the bound and free analyte fractions (with the sample analyte). The amount of bound labelled analyte is measured as an indirect measure of the analyte concentration in the original sample. In a variation of "competitive" immunoassay design a labelled antibody is employed, together with a solid phase analyte (or analyte analogue) preparation. The binding of the labelled antibody is distributed between the sample analyte and the solid phase analyte (or analyte analogue). The amount of antibody bound to the solid phase analyte (or analyte analogue) preparation is used as an indirect measure of the analyte concentration of the sample.

According to a third embodiment of the invention there is provided a method for detecting and measuring a nucleotide, including a nucleosome associated nucleotide, in a sample by a label-free immunometric immunoassay which comprises the steps of:
(i) contacting the sample with an antibody or other binder which binds to a nucleotide;
(ii) detecting and/or quantifying the binding of said antibody or other binder to a nucleotide in the sample; and
(iii) using the presence or degree of such binding as a measure of the presence of a nucleotide in the sample.

According to a fourth embodiment of the invention there is provided a method for detecting and measuring a nucleotide, including a nucleosome associated nucleotide, in a sample by a competitive immunoassay which comprises the steps of:
(i) contacting the sample with an antibody or other binder which binds to a nucleotide;
(ii) detecting and/or quantifying the binding of said antibody or other binder to a nucleotide in the sample; and
(iii) using the presence or degree of such binding as a measure of the presence of a nucleotide in the sample.

It will be clear to those skilled in the art that these immunoassay methods of the invention measure nucleosomes and nucleosome associated nucleotides directly without any requirement for extraction of DNA. In contrast, nucleotide immunoassay methods of the current art detect (non-nucleosome associated) nucleotides after extraction of DNA from a sample. The methods of the invention have advantages of speed, simplicity and suitability for direct measurements in complex biological samples including blood or its derivatives.

According to a fifth embodiment of the invention there is provided a method for detecting the proportion of cell free DNA that comprises a particular nucleotide in a sample comprising the steps of:
(i) detecting or measuring the level of cell free DNA in a sample;
(ii) detecting or measuring the level of a nucleosome associated nucleotide according to a method of the invention; and
(iii) using the two measurements to determine the proportion of DNA that comprises the nucleotide.

According to one embodiment of this aspect of the invention; both the cell free DNA level in the sample and the nucleotide of interest are measured using the method of the invention. In another embodiment the nucleotide of interest is a methylated cytosine nucleotide and the proportion of the DNA that comprises the nucleotide provides a measure of global DNA methylation.

We have shown that the detection and measurement of nucleosomes containing nucleotides in the blood taken from subjects can be used as a diagnostic method to identify subjects with cancer and to differentiate them from healthy subjects. Furthermore we have shown that the patterns of nucleosomes containing a panel of different nucleotides, histone variants and histone PTMs can be used to distinguish between different cancers. It will be clear to those skilled in the art that this provides a cancer blood test that will detect cancer in subjects and can be used to distinguish between cancer types in cancer positive subjects. According to a further aspect of the invention there is provided a method for detecting or diagnosing the presence of a disease by measuring or detecting the presence and/or the level or concentration of cell free nucleosomes containing a nucleotide in a body fluid, and using the detected level as a biomarker of the disease status of a subject including, without limitation, a clinical diagnosis of a disease, a differential diagnosis of disease type or subtype, or a disease prognosis, or a disease relapse, or a diagnosis of subject susceptibility to treatment regimens. It will be appreciated by those skilled in the art that body fluids used for diagnostic testing include without limitation blood, serum, plasma, urine, cerebrospinal fluid and other fluids. In a preferred embodiment the body fluid selected as the sample is blood, serum or plasma. The assay response, level, concentration or quantity of a nucleosome associated nucleotide in a body fluid may be expressed in absolute terms or relative terms, for example without limitation as a proportion of the total nucleosome level present or as a ratio to the level of nucleosomes containing another nucleotide or histone variant or histone PTM or to the level of total DNA.

In one embodiment of the invention the nucleosome associated nucleotide measurement is used as a member of a diagnostic panel of tests or measurements for the detection or diagnosis of the disease status of a subject including, without limitation, a clinical diagnosis of a disease, a differential diagnosis of disease type or subtype, or a disease prognosis, or a disease relapse, or a diagnosis of subject susceptibility to treatment regimens As all or most circulating cell free DNA is reported to exist as nucleosome associated DNA, it will be clear to those skilled in the art that diagnosis or detection of disease state can be achieved by detection or measurement of nucleotides per se using a direct nucleotide immunoassay of the invention with no DNA extraction step in a biological fluid, rather than, or in addition to, an immunoassay for nucleosome associated nucleotides. According to a further aspect of the invention there is provided a non-extraction nucleotide immunoassay method for detecting or diagnosing the presence of a disease by measuring or detecting the presence and/or the level or concentration of a nucleotide in a body fluid, and using the detected level as a biomarker (either alone as a member of a panel of tests) of the disease status of a subject including, without limitation, a clinical diagnosis of a disease, a differential diagnosis of disease type or subtype, or a disease prognosis, or a disease relapse, or a diagnosis of subject susceptibility to treatment regimens. It will be appreciated by those skilled in the art that body fluids used for diagnostic testing include without limitation blood, serum, plasma, urine, cerebrospinal fluid and other fluids. In a preferred embodiment the body fluid selected as the sample is blood, serum or plasma. The assay response, level, concentration or quantity of a nucleotide in a body fluid may be expressed in absolute terms or relative terms, for example without limitation as a proportion of the total nucleosome level present or as a ratio to the level of another nucleotide or histone variant or histone PTM or to the level of total DNA.

According to a further aspect of the invention there is provided a method for detecting or measuring the presence and/or the level of nucleosomes containing a nucleotide in a cell which comprises the steps of:
(i) isolating chromatin from a cell;
(ii) breaking down the chromatin to form mono-nucleosomes and/or oligo-nucleosomes; and
(iii) detecting or measuring the presence of a nucleotide in the mono-nucleosomes and/or oligo-nucleosomes by means of an immunoassay method of the invention.

Methods for producing mono-nucleosomes and/or oligo-nucleosomes from chromatin are well known in the art and include enzyme digestion and sonication (Dai et al, 2011). In one embodiment the nucleotide selected for detection by the method is a commonly occurring nucleotide that occurs in all or most intact nucleosomes, providing a method for the detection or measurement of nucleosomes per se. In another embodiment the nucleotide selected for detection by the method is a commonly occurring nucleotide that occurs in all or most intact nucleosomes, providing a method for the detection or measurement of nucleosome bound DNA.

It will be appreciated by those skilled in the art that the described method of detecting nucleosome associated nucleotides in cells or tissues has advantages over currently used methods including IHC, or detecting nucleotides in DNA extracted from cells by restriction digestion and nearest-neighbour analysis, or by fluorescent assays using chloracetaldehyde, or by inverse determination by methylation of all CpG sites using DNA methyltransferase in conjunction with tritium-labeled S-adenosyl methionine to calculate the amount of unmethylated CpG, or by digestion of DNA into single nucleotides for analysis by high-performance liquid chromatography, thin-layer chromatography, or liquid chromatography followed by mass spectroscopy. The level, concentration or quantity of a particular nucleosome associated nucleotide may be expressed in absolute terms or relative terms, for example as a proportion of the total nucleosomes present or as a ratio to the total level of nucleosomes or to the level of nucleosomes containing another nucleotide or histone variant or histone PTM, or to the total level of DNA.

It will be clear to those skilled in the art that the terms antibody, binder or ligand in regard to any aspect of the invention is not limiting but intended to include any binder capable of binding to particular molecules or entities and that any suitable binder can be used in the method of the invention. It will also be clear that the term nucleosomes is intended to include mononucleosomes and oligonucleosomes and any such chromatin fragments that can be analysed in fluid media.

According to another aspect of the invention there is provided a kit for detecting or measuring nucleosomes which comprises a ligand or binder specific for the nucleotide or a component part thereof, or a structural/shape mimic of the nucleosome or component part thereof, together with instructions for use of the kit in accordance with any of the methods defined herein.

According to a further aspect of the invention there is provided a kit for detecting or measuring nucleosomes containing a nucleotide which comprises a ligand or binder specific for the nucleotide or a component part thereof, or a structural/shape mimic of the nucleotide or component part thereof, together with instructions for use of the kit in accordance with any of the methods defined herein.

According to another aspect of the invention there is provided a method for identifying a nucleosome associated nucleotide biomarker or a nucleotide biomarker for detecting or diagnosing disease status in animals or humans which comprises the steps of:
  (i) detecting or measuring the level of cell free nucleosomes containing a nucleotide in a body fluid of diseased subjects;
  (ii) detecting or measuring the level of cell free nucleosomes containing a nucleotide in a body fluid of control subjects; and
  (iii) using the difference between the levels detected in diseased and control subjects to identify whether a nucleotide is useful as a biomarker for that disease.

It will be clear to those skilled in the art that the control subjects may be selected on a variety of basis which may include, for example, subjects known to be free of the disease or may be subjects with a different disease (for example; for the investigation of differential diagnosis).

According to a further aspect of the invention there is provided a method for identifying a nucleosome associated nucleotide biomarker or a nucleotide biomarker for assessing the prognosis of a diseased animal or human subject which comprises the steps of:
  (i) detecting or measuring the level of cell free nucleosomes containing a nucleotide in a body fluid of diseased subjects; and
  (ii) correlating the level of cell free nucleosomes containing a nucleotide detected in a body fluid of diseased subjects with the disease outcome of the subjects.

According to a further aspect of the invention there is provided a method for identifying a nucleotide biomarker to be used for the selection of a treatment regimen for a diseased animal or human subject in need of treatment which comprises the steps of:
  (i) detecting or measuring the level of cell free nucleosomes containing a nucleotide in a body fluid of diseased subjects; and
  (ii) correlating the level of cell free nucleosomes containing a nucleotide detected in a body fluid of diseased subjects with the observed efficacy of a treatment regimen in those subjects.

According to a further aspect of the invention there is provided a method for identifying a nucleosome associated nucleotide biomarker or a nucleotide biomarker to be used for monitoring the treatment of a diseased animal or human subject which comprises the steps of:
  (i) detecting or measuring the level of cell free nucleosomes containing a nucleotide in a body fluid of a diseased subject;
  (ii) repeating said detection or measurement on one or more occasions during the disease progression of the subject; and
  (iii) correlating the level of cell free nucleosomes containing a nucleotide detected in a body fluid of a diseased subject with the disease progression in the subject.

According to a further aspect of the invention, there is provided a biomarker identified by the method as defined herein.

It is known in the art that one may detect the presence of a moiety that is comprised as part of a complex containing other moieties by immunoassay methods. It will be clear to those skilled in the art that cell free nucleosomes containing a nucleotide can be detected in a biological fluid including blood, plasma, serum and urine by a procedure involving the direct immunoassay of the nucleotide itself in the fluid. In this procedure a single antibody immunoassay, utilising an antibody directed to an epitope present on a nucleotide, or a 2-site immunoassay, utilising two antibodies directed to two epitopes present on a nucleotide, is used to detect the presence of a nucleotide within a nucleosome. Thus in another embodiment of the invention a nucleotide contained within a nucleosome is detected directly in a biological fluid including blood, plasma, serum and urine by use of an immunoassay method for a nucleotide.

Thus in one embodiment of the invention a nucleosome associated nucleotide is detected directly without prior extraction in a biological fluid including blood, plasma, serum and urine using an immunoassay for the nucleotide.

A further aspect of the invention provides ligands or binders, such as naturally occurring or chemically synthesised compounds, capable of specific binding to the biomarker. A ligand or binder according to the invention may comprise a peptide, an antibody or a fragment thereof, or a synthetic ligand such as a plastic antibody, or an aptamer or oligonucleotide, capable of specific binding to the biomarker. The antibody can be a monoclonal antibody or a fragment thereof capable of specific binding to the biomarker. A ligand according to the invention may be labeled with a detectable marker, such as a luminescent, fluorescent, enzyme or radioactive marker; alternatively or additionally a ligand according to the invention may be labelled with an affinity tag, e.g. a biotin, avidin, streptavidin or His (e.g. hexa-His) tag. Alternatively ligand binding may be determined using a label-free technology for example that of ForteBio Inc.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the biomarker. In these uses, the detection and/or quantification can be performed on a biological sample as defined herein.

Diagnostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

A further aspect of the invention is a kit for detecting the presence of a disease state, comprising a biosensor capable of detecting and/or quantifying one or more of the biomarkers as defined herein.

Biomarkers for detecting the presence of a disease are essential targets for discovery of novel targets and drug molecules that retard or halt progression of the disorder. As the level of the biomarker is indicative of disorder and of drug response, the biomarker is useful for identification of novel therapeutic compounds in in vitro and/or in vivo assays. Biomarkers of the invention can be employed in methods for screening for compounds that modulate the activity of the biomarker.

Thus, in a further aspect of the invention, there is provided the use of a binder or ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the biomarker in a subject, comprising administering a test substance to a subject animal and detecting and/or quantifying the level of the biomarker present in a test sample from the subject.

The term "biomarker" means a distinctive biological or biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

The terms "detecting" and "diagnosing" as used herein encompass identification, confirmation, and/or characterisation of a disease state. Methods of detecting, monitoring and of diagnosis according to the invention are useful to confirm the existence of a disease, to monitor development of the disease by assessing onset and progression, or to assess amelioration or regression of the disease. Methods of detecting, monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), and reducing relapse rates.

In one embodiment, said biomarker is released from the cells of a tumour. Thus, according to a further aspect of the invention there is provided a method for the detection of a tumour growth which comprises the steps of (i) measuring a biomarker in a biological sample that is associated with or released from the cells of a tumour and (ii) demonstrating that the level of said biomarker is associated with the size, stage, aggressiveness or dissemination of the tumour.

It is known that increased cell turnover, cell death and apoptosis lead to increased circulatory levels of cell free nucleosomes (Holdenrieder et al, 2001). Circulating cell free nucleosomes level is a non-specific indicator and occurs in a variety of conditions including inflammatory diseases, a large variety of benign and malignant conditions, autoimmune diseases, as well as following trauma or ischaemia (Holdenrieder et al 2001). It will be clear to those skilled in the art that the invention will have application in a variety of disease areas where circulating nucleosomes have been found in subjects. These include, without limitation, trauma (for example; severe injury or surgery), extreme exercise (for example running a marathon), stroke and heart attack, sepsis or other serious infection and endometriosis. We have used the immunoassay method of the invention to measure nucleosome levels and investigate their nucleotide and histone structure variability in a variety of such diseases including cardiomyopathy, systemic lupus erythematosus, ulcerative colitis, chronic obstructive pulmonary disease, Crohn's disease and rheumatoid arthritis and compared these with the results of healthy subjects. We can detect nucleosomes and determine their relative structures (in terms of histone and nucleotide composition) in all these diseases. As methods of the current invention are capable of detection of a wider range of nucleosomes than current nucleosome ELISA methods, the methods of the invention have applications in a wide range of cancer and non-cancer disease areas.

The immunoassays of the invention include immunometric assays employing enzyme detection methods (for example ELISA), fluorescence labelled immunometric assays, time-resolved fluorescence labelled immunometric assays, chemiluminescent immunometric assays, immunoturbidimetric assays, particulate labelled immunometric assays and immunoradiometric assays and competitive immunoassay methods including labelled antigen and labelled antibody competitive immunoassay methods with a variety of label types including radioactive, enzyme, fluorescent, time-resolved fluorescent and particulate labels. All of said immunoassay methods are well known in the art, see for example Salgame et al, 1997 and van Nieuwenhuijze et al, 2003.

In one embodiment, said biological sample comprises a body fluid. For example, biological samples that may be tested in a method of the invention include cerebrospinal fluid (CSF), whole blood, blood serum, plasma, menstrual blood, endometrial fluid, urine, saliva, or other bodily fluid (stool, tear fluid, synovial fluid, sputum), breath, e.g. as condensed breath, or an extract or purification therefrom, or dilution thereof. Biological samples also include specimens from a live subject, or taken post-mortem. The samples can be prepared, for example where appropriate diluted or concentrated, and stored in the usual manner.

In one embodiment, the method of the invention is repeated on multiple occasions. This embodiment provides the advantage of allowing the detection results to be monitored over a time period. Such an arrangement will provide the benefit of monitoring or assessing the efficacy of treatment of a disease state. Such monitoring methods of the invention can be used to monitor onset, progression, stabilisation, amelioration, relapse and/or remission.

Thus, the invention also provides a method of monitoring efficacy of a therapy for a disease state in a subject, suspected of having such a disease, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the nature or amount of the biomarker(s) in test samples taken on different occasions.

Thus, according to a further aspect of the invention, there is provided a method for monitoring efficacy of therapy for a disease state in a human or animal subject, comprising:
(i) quantifying the amount of the biomarker as defined herein; and
(ii) comparing the amount of said biomarker in a test sample with the amount present in one or more control (s) and/or one or more previous test sample(s) taken at an earlier time from the same test subject.

A change in the level of the biomarker in the test sample relative to the level in a previous test sample taken earlier from the same test subject may be indicative of a beneficial effect, e.g. stabilisation or improvement, of said therapy on the disorder or suspected disorder. Furthermore, once treatment has been completed, the method of the invention may be periodically repeated in order to monitor for the recurrence of a disease.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

In a further embodiment the monitoring of more rapid changes due to fast acting therapies may be conducted at shorter intervals of hours or days.

According to a further aspect of the invention, there is provided a method for identifying a biomarker for detecting the presence of a disease state. The term "identifying" as used herein means confirming the presence of the biomarker present in the biological sample. Quantifying the amount of the biomarker present in a sample may include determining the concentration of the biomarker present in the sample. Identifying and/or quantifying may be performed directly on the sample, or indirectly on an extract therefrom, or on a dilution thereof.

In alternative aspects of the invention, the presence of the biomarker is assessed by detecting and/or quantifying antibody or fragments thereof capable of specific binding to the biomarker that are generated by the subject's body in response to the biomarker and thus are present in a biological sample from a subject having a disease state.

Identifying and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the biomarker in the sample or samples. Biological samples that may be tested in a method of the invention include those as defined hereinbefore. The samples can be prepared, for example where appropriate diluted or concentrated, and stored in the usual manner.

Identification and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length. It is noted in particular that peptides of the same or related sequence to that of histone tails are particularly useful fragments of histone proteins.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand or binder may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample by SELDI TOF or MALDI TOF to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Identifying and/or quantifying the analyte biomarkers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immuno-precipitation and any particle-based immunoassay (e.g. using gold, silver, or latex particles, magnetic particles, or Q-dots). Immunological methods may be performed, for example, in microtitre plate or strip format.

In one embodiment, one or more of the biomarkers may be replaced by a molecule, or a measurable fragment of the molecule, found upstream or downstream of the biomarker in a biological pathway.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, identifying and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

As used herein, the term "biosensor" means anything capable of detecting the presence of the biomarker. Examples of biosensors are described herein.

Biosensors according to the invention may comprise a ligand binder or ligands, as described herein, capable of specific binding to the biomarker. Such biosensors are useful in detecting and/or quantifying a biomarker of the invention.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect one or more biomarkers of the invention include acoustic, plasmon resonance, holographic, Bio-Layer Interferometry (BLI) and microengineered sensors. Imprinted recognition elements, thin film transistor technology, magnetic acoustic resonator devices and other novel acousto-electrical systems may be employed in biosensors for detection of the one or more biomarkers of the invention.

Methods involving identification and/or quantification of one or more biomarkers of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-medicine.

Diagnostic kits for the diagnosis and monitoring of the presence of a disease state are described herein. In one embodiment, the kits additionally contain a biosensor capable of identifying and/or quantifying a biomarker. Suitably a kit according to the invention may contain one or more components selected from the group: a ligand binder, or ligands, specific for the biomarker or a structural/shape mimic of the biomarker, one or more controls, one or more reagents and one or more consumables; optionally together with instructions for use of the kit in accordance with any of the methods defined herein.

The identification of biomarkers for a disease state permits integration of diagnostic procedures and therapeutic regimes. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, not achievable using the current measures.

Furthermore, diagnostic biomarker tests are useful to identify family members or patients with mild or asymptomatic disease or who may be at high risk of developing symptomatic disease. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder. If pharmacological treatment is assessed to be inadequate, then therapy can be reinstated or increased; a change in therapy can be given if appropriate. As the biomarkers are sensitive to the state of the disorder, they provide an indication of the impact of drug therapy.

The invention will now be illustrated with reference to the following non-limiting examples.

Example 1

Figure 1:
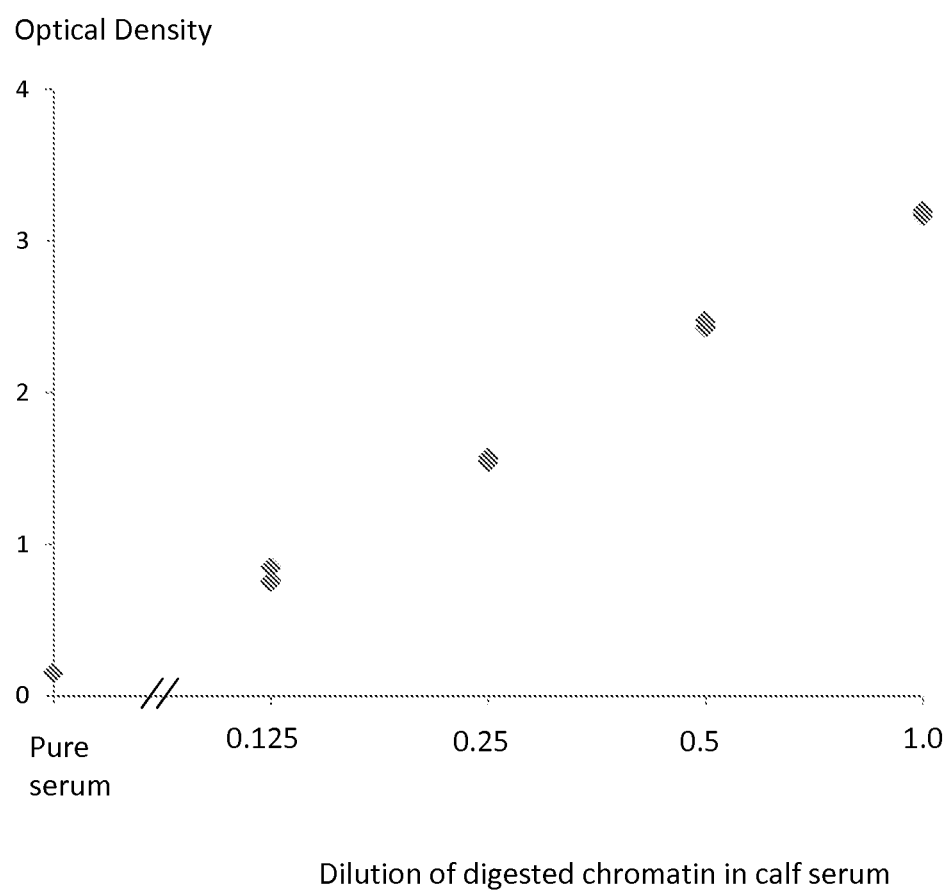
FIG. 1. ELISA dose response curve for the detection of 5-methylcytosine methylated DNA in cell free nucleosomes in cross-linked digested chromatin extracted from MCF7 cells diluted into calf serum.

A commercially available nucleosome preparation produced by digestion of chromatin extracted from MCF7 cells in which the DNA and proteins in the nucleosome are cross-linked for stability (ensuring that all histones present in the preparation are incorporated into intact nucleosomes) was assayed for methylated DNA using an ELISA method for the nucleosome associated nucleotide 5-methylcytosine using a solid phase anti-histone capture antibody that binds intact nucleosomes and a biotinylated monoclonal anti-5-methylcytosine detection antibody. The nucleosome sample was serially diluted in fetal calf serum and was tested in duplicate in the ELISA. Neat fetal calf serum was also run in the ELISA as a control sample containing no cell free nucleosomes. The assay method was as follows: A solution of anti-histone antibody in 0.1 M phosphate buffer pH 7.4 was added to microtitre wells (100 µL/well) and incubated overnight at 4° C. to coat the wells with capture antibody. Excess anti-histone antibody was decanted. A solution of bovine serum albumin (20 g/L) was added to the wells (200 µL/well) and incubated 30 minutes at room temperature to block excess protein binding sites on the wells. Excess bovine serum albumin solution was decanted and the wells were washed three times with wash buffer (200 µL/well, 0.05 M TRIS/HCl buffer pH 7.5 containing 1% Tween 20). Sample (10 µL/well) and assay buffer (50 µL/well, 0.05 M TRIS/HCl pH 7.5 containing 0.9% NaCl, 0.05% sodium deoxycholate and 1% Nonidet P40 substitute) were added to the wells incubated 90 minutes at room temperature with mild agitation. The sample and assay buffer mixture was decanted and the wells were washed three times with wash buffer (200 µL/well). A solution of biotinylated anti-5-methylcytosine detection antibody was added (50 µL/well) and incubated 90 minutes at room temperature with mild agitation. Excess detection antibody was decanted and the wells were again washed three times with wash buffer (200 µL/well). A solution containing a streptavidin-horse radish peroxidase conjugate was added (50 µL/well) and incubated 30 minutes at room temperature with mild agitation. Excess conjugate was decanted and the wells were again washed three times with wash buffer (200 µL/well). A coloured substrate solution (100 µL/well, 2,2'-Azinobis [3-ethylbenzothiazoline-6-sulfonic acid]-diammonium salt) was added and incubated 20 minutes at room temperature with mild agitation. The optical density (OD) of the wells was measured at a wavelength of 405 nm using a standard microtitre plate reader. A dose response curve of increasing colour with increasing nucleosome associated anti-5-methylcytosine concentration was observed with a low background signal observed in the absence of 5-methylcytosine (fetal calf serum). The positive ELISA signal indicates that the 5-methylcytosine detected by the ELISA is incorporated within an intact nucleosome comprising both histone protein and DNA as (i) the capture antibody binds to histones in the sample and (ii) detection antibody binds to the 5-methylcytosine component of DNA. The results are shown in FIG. 1.

Example 2

Figure 2:
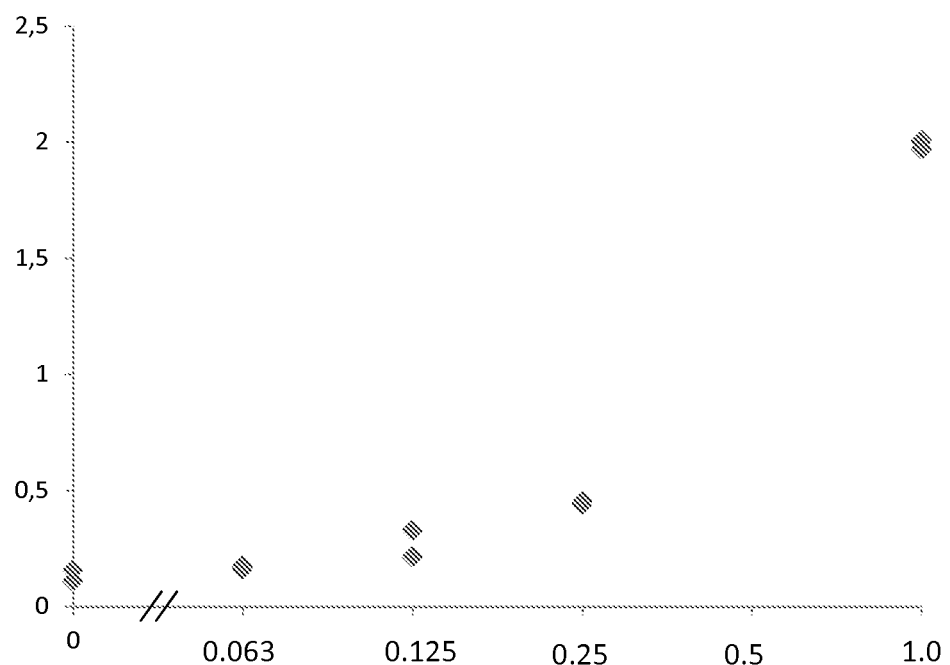
FIG. 2. ELISA dose response curve for the detection of 5-hydroxymethylcytosine methylated DNA in cell free nucleosomes in cross-linked digested chromatin extracted from A375 cells diluted into calf serum.

A commercially available nucleosome preparation produced by digestion of chromatin extracted from A375 cells in which the DNA and proteins in the nucleosome are cross-linked for stability (ensuring that all histones present in the preparation are incorporated into intact nucleosomes) was assayed for 5-hydroxymethylated DNA using an ELISA method for the nucleosome associated nucleotide 5-hydroxymethylcytosine using a solid phase anti-histone capture antibody that binds intact nucleosomes and a biotinylated monoclonal anti-5-hydroxymethylcytosine detection antibody. The nucleosome sample was serially diluted in fetal calf serum and was tested in duplicate in the ELISA. Neat fetal calf serum was also run in the ELISA as a control sample containing no cell free nucleosomes. The assay method was as follows: A solution of anti-histone antibody in 0.1 M phosphate buffer pH 7.4 was added to microtitre wells (100 µL/well) and incubated overnight at 4° C. to coat the wells with capture antibody. Excess anti-histone antibody was decanted. A solution of bovine serum albumin (20 g/L) was added to the wells (200 µL/well) and incubated 30 minutes at room temperature to block excess protein binding sites on the wells. Excess bovine serum albumin solution was decanted and the wells were washed three times with wash buffer (200 µL/well, 0.05 M TRIS/HCl buffer pH 7.5 containing 1% Tween 20). Sample (10 µL/well) and assay buffer (50 µL/well, 0.05 M TRIS/HCl pH 7.5 containing 0.9% NaCl, 0.05% sodium deoxycholate and 1% Nonidet P40 substitute) were added to the wells incubated 90 minutes at room temperature with mild agitation. The sample and assay buffer mixture was decanted and the wells were washed three times with wash buffer (200 µL/well). A solution of biotinylated anti-5-hydroxymethylcytosine detection antibody was added (50 µL/well) and incubated 90 minutes at room temperature with mild agitation. Excess detection antibody was decanted and the wells were again washed three times with wash buffer (200 µL/well). A solution containing a streptavidin-horse radish peroxidase conjugate was added (50 µL/well) and incubated 30 minutes at room temperature with mild agitation. Excess conjugate was decanted and the wells were again washed three times with wash buffer (200 µL/well). A coloured substrate solution (100 µL/well, 2,2'-Azinobis [3-ethylbenzothiazoline-6-sulfonic acid]-diammonium salt) was added and incubated 20 minutes at room temperature with mild agitation. The optical density (OD) of the wells was measured at a wavelength of 405 nm using a standard microtitre plate reader. A dose response curve of increasing colour with increasing nucleosome associated 5-hydroxymethylcytosine concentration was observed with a low background signal observed in the absence of 5-hydroxymethylcytosine (fetal calf serum). The positive ELISA signal indicates that the 5-hydroxymethylcytosine detected by the ELISA is incorporated within an intact nucleosome comprising both histone protein and DNA as (i) the capture antibody binds to histones in the sample and (ii) detection antibody binds to the 5-hydroxymethylcytosine component of DNA. The results are shown in FIG. 2.

Example 3

We used two nucleosome ELISA methods of the current art to measure the circulating cell free nucleosome content of serum and plasma blood samples taken from 20 healthy subjects. The first current ELISA method (ELISA 1) was the Roche Cell Death ELISA and the other (ELISA 2) an ELISA employing an anti-histone capture antibody and an anti-histone-DNA complex detection antibody. The nucleosome levels detected by both current nucleosome ELISA methods were lower in normal plasma than in normal serum. The normal range (expressed in optical density units) for the serum level of nucleosomes was calculated (mean±2 standard deviations of the mean of the 20 healthy subject serum results) to be 0-4.3 OD units for ELISA 1 and 0-1.4 for ELISA 2. The respective ranges for plasma were 0-0.95 and 0-0.96. The results are shown in FIG. 3.

We also measured the levels of nucleosomes containing the two nucleosome associated nucleotides as well as 3 nucleosome associated histone variants and a histone PTM in the same 20 samples taken from healthy subjects. The results show that the healthy serum samples have uniformly low levels of nucleosomes containing histone variants or PTM or nucleotides. The normal ranges (expressed as optical density) for the serum level of nucleosomes containing histone variants, PTM or nucleotides were; (a) 0-0.36 for mH2A1.1, (b) 0.05-0.78 for mH2A2, (c) 0.11-0.58 for H2AZ, (d) 0.06-0.61 for P-H2AX(Ser139), (e) 0.06-0.36 for 5-methylcytosine and (f) 0.03-0.36 for 5-hydroxymethylcytosine. The measured EDTA plasma results were higher for all 20 healthy subjects. The results are shown in FIGS. 4, 5, 6, 7, 8 and 9.

Example 4

We measured cell free nucleosomes containing 5-methylcytosine in EDTA plasma taken from 13 healthy subjects and 55 subjects with cancer of the stomach, large intestine, rectum, lung (small cell carcinoma and various non-small cell carcinomas), breast, ovary, pancreas, prostate, kidney and various oral cancers (oral cavity, palate, pharynx and larynx). All of the 13 samples from healthy subjects were positive for one or more cell free nucleosome type. All of the 55 samples from cancer patients were positive for all the cell free nucleosome types assayed. However, the levels detected in samples taken from cancer subjects were higher than found in samples from healthy subjects and the results showed that healthy and cancer subjects can be discriminated. For example the normal range calculated in OD terms as the mean±2 standard deviations of the mean, for nucleosome associated 5-methylcytosine 0-1.41. Using this cut-off value all 13 healthy samples were negative and 30 of the 55 cancer samples were positive (an overall clinical sensitivity of 55%) including 38% (3 of 8) of stomach, 60% (3 of 5) of large intestinal, 33% (1 of 3) of rectal, 33% (2 of 6) of small cell lung, 64% (9 of 14) of non-small cell lung, 33% (2 of 6) of breast, 100% (1 of 1) of ovarian, 100% (1 of 1) of pancreas, 33% (2 of 6) of prostate, 100% (1 of 1) of kidney and 60% (3 of 5) of oral cancer samples. The results are shown in FIG. 17.

We also used the methods of the invention to measure a variety of other nucleosome associated structures in the same samples. The results of these immunoassays were compiled to provide a profile of nucleosome structures in samples taken from cancer patients normalised relative to detected levels of nucleosomes containing 5-methylcytosine. We compared the resulting profiles to the nucleosome structure of samples taken from healthy subjects. The nucleosome structure profile of cell free nucleosomes was found to be different to those of healthy subjects. The results are shown in FIG. 20. We similarly compiled nucleosome structure profiles for samples taken from a variety of non-cancer diseases and compared these to the profile of nucleosomes in samples taken from cancer patients and from healthy subjects. The results are shown in FIG. 21.

Figure 18:
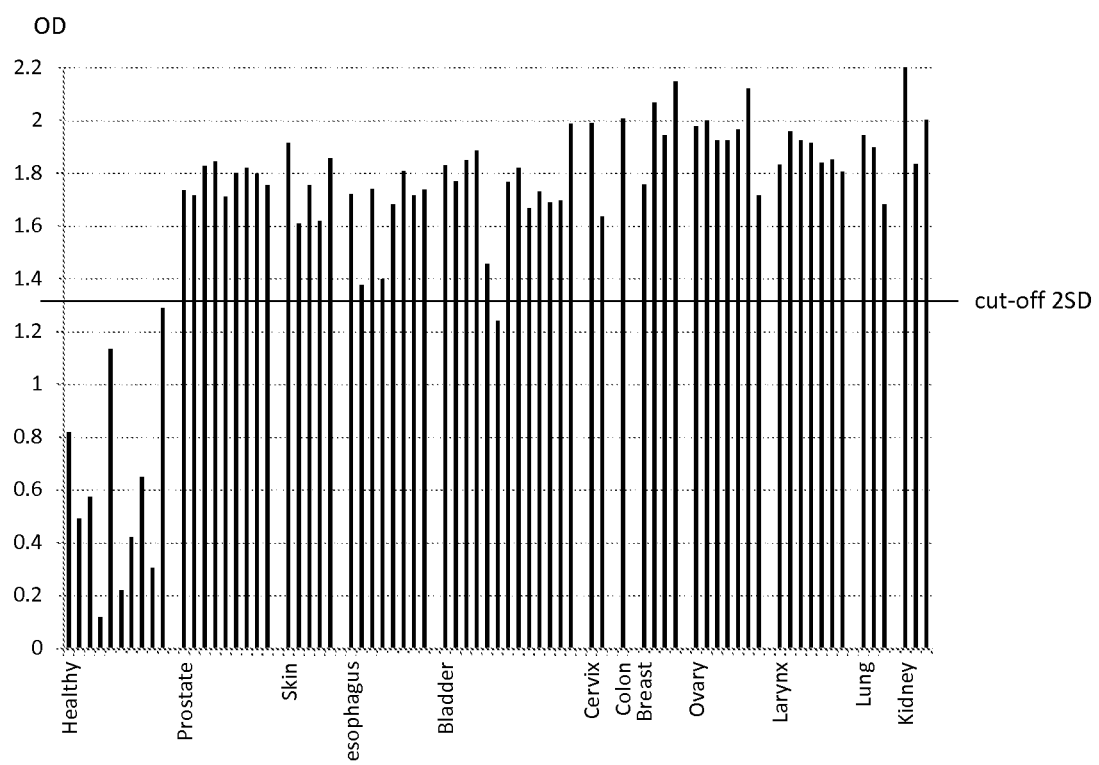
FIG. 18. Cell free nucleosome associated 5-methylcytosine levels detected for EDTA plasma samples taken from 10 healthy volunteers and 61 cancer patients. The cut-off point defined as the mean value of the healthy samples plus two standard deviations in the mean is shown.

We then performed another similar experiment including samples from 10 healthy subjects and a further 62 patients with cancer of various types. The results were similar to the first experiment. For example using the results for nucleosome associated 5-methylcytosine and a cut-off of mean+2 standard deviations of the mean of the results for healthy subjects, negative results were obtained for all 10 healthy subjects and positive results were obtained for 95% (61 of 62) of cancer patients including 9 of 9 prostate cancer patients, 5 of 5 skin cancer patients, 8 of 8 esophagus cancer patients, 12 of 13 bladder cancer patients, 2 of 2 cervix cancer patients and 1 of 1 colon cancer patients, 4 of 4 breast cancer patients, 7 of 7 ovary cancer patients, 7 of 7 larynx cancer patients, 3 of 3 lung cancer patients and 3 of 3 renal cancer patients. The results are shown in FIG. 18. This result indicates that serum nucleotide levels and nucleosome associated nucleotides levels, including particularly 5-methylcytosine, are clinically sensitive biomarkers for cancer.

Example 5

We used two nucleosome ELISA methods of the current art to measure the circulating cell free nucleosome content of samples taken from 3 subjects with colon cancer, 13 subjects with lung cancer, 2 subjects with pancreatic cancer, 1 subject with oral cancer and a nucleosome sample produced from healthy subjects according to the method of Holdenrieder (*Holdenrieder et al, 2001). The first current ELISA method (ELISA 1) was the Roche Cell Death ELISA and the other (ELISA 2) an ELISA employing an anti-histone capture antibody and an anti-histone-DNA complex detection antibody.

We also measured the levels of nucleosomes containing the nucleotides 5-methylcytosine and 5-hydroxymethylcytosine as a well as three variant histones and a histone PTM in the same 19 samples taken from cancer subjects. The results show that, although low nucleosome results for ELISA methods of the current art were detected for most subjects, particularly for pancreatic and oral cancer patients, most of these samples have higher detectable levels of nucleosomes that contain one or more nucleosome associated nucleotides or variant histones. The results for samples taken from 3 subjects with colon cancer, 13 subjects with lung cancer, 2 subjects with pancreatic cancer and 1 subject with oral cancer are shown in FIGS. 10, 11, 12, and 13 respectively. Significant nucleosome associated histone variant levels and histone PTM levels were detected in 16 of the 19 cancer samples (all but 3 lung cancer samples). In addition significant nucleosome associated 5-hydroxymethylcytosine levels were detected in 12 of the 19 cancer samples. Furthermore, significant nucleosome associated 5-methylcytosine levels were detected in all 19 cancer samples.

Figure 14:
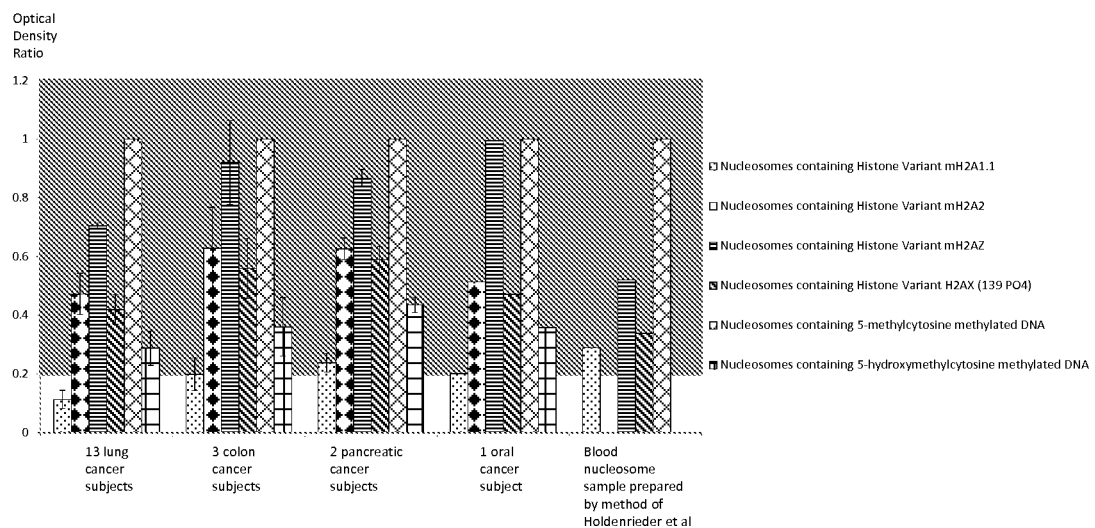
FIG. 14. Cell-free nucleosome associated levels of nucleotides and types of histones detected for EDTA plasma samples taken from 4 different cancer diseases normalised as a proportion of nucleosome associated 5-methylcytosine methylated DNA levels detected using ELISA methods of the invention. Normalised levels for a sample containing nucleosomes from healthy volunteers produced by the method of *Holdenrieder et al 2001 is shown for comparison (mH2A2 and 5-hydroxymethylcytosine were not measured for this sample).

Furthermore the pattern of nucleosome levels containing different nucleotide, histone variant and histone PTM levels is not uniform for all subjects but displays different patterns for different cancers tested. To facilitate comparison between results for subjects with the same or different cancers; the results for the nucleosome tests (for nucleosomes containing macroH2A1.1, macroH2A2, H2AZ, P-H2AX(Ser139), 5-methylcytosine, 5-hydroxymethylcytosine) were normalised as a proportion of the OD signal observed for nucleosomes containing 5-methylcytosine. The normalised results (with error bars showing the standard deviation in results where samples from more than one subject were tested) are shown for each cancer in FIG. 14 as well as the same results for the nucleosome sample produced from healthy subjects (mH2A2 and 5-hydroxymethylcytosine were not measured for this sample). FIG. 14 shows that the distribution pattern of nucleosomes containing the different normalised nucleotides, histone variants or PTM in all four cancers investigated differs quite markedly to the distribution of nucleosomes in the sample prepared from healthy subjects. For example the relative level of nucleosomes containing macroH2A1.1 in the healthy nucleosome sample differs from that detected in the samples of any of the cancer types. Thus the present invention can be used as a method for the detection of cancer in a simple blood based screening test. It will be clear to those skilled in the art that the invention includes the testing of nucleosomes containing other further nucleotides and/or histone variants and/or histone modifications to further or better discriminate between circulating cell free nucleosomes of tumour or other disease origin.

Furthermore the pattern of nucleosome types observed differs for different cancer types. For example; the samples taken from subjects with colon, pancreatic and oral cancer can be distinguished by different normalised levels of nucleosome associated H2AZ and 5-hydroxymethylcytosine. Similarly oral cancer has different normalised levels of both nucleosomes containing mH2A2 or P-H2AX(Ser139) than any of the other three cancer types and samples from subjects with pancreatic cancer can be distinguished from samples from subjects with colon cancer on the basis of a different relative level of nucleosomes containing variant macroH2A1.1. Thus the present invention can be used as a method to diagnose cancer generally and to distinguish a particular cancer type. It will be clear to those skilled in the art that the invention includes the testing of nucleosomes containing other further histone variants and/or histone modifications and/or nucleotides to further or better discriminate between circulating cell free nucleosomes of different specific tumour origin or other disease origin.

Example 6

We tested the method of the invention in serum samples taken from 3 healthy subjects and from 10 colon cancer patients. We measured nucleosomes containing 5-methylcytosine in these samples and the cancer results were uniformly elevated over the results obtained for healthy subjects as shown in FIG. 16.

Example 7

We measured the nucleosome associated 5-methylcytosine levels of human EDTA plasma samples taken from lung and colon cancer patients. The levels detected were correlated with the disease progression of the patients. The results shown in FIG. 19 indicate that nucleosome associated 5-methylcytosine levels increase with severity of disease in terms of size, stage, nodal spread and nucleosome associated 5-methylcytosine levels may be used, alone or as part of a diagnostic panel, as indicators of disease progression,

REFERENCES

Allen et al, A simple method for estimating global DNA methylation using bisulfite PCR of repetitive DNA elements. Nucleic Acids Research: 32(3) e38DOI: 10.1093/nar/gnh032

Bawden et al, Detection of histone modification in cell-free nucleosomes. WO 2005/019826, 2005

Boulard et al, Histone variant macroH2A1 deletion in mice causes female-specific steatosis. Epigenetics & Chromatin: 3(8), 1-13, 2010 Cell Biolabs, Inc. Product Manual for "Global DNA Methylation ELISA Kit (5'-methyl-2'-deoxycytidine Quantitation", 2011

Dai et al, Detection of Post-translational Modifications on Native Intact Nucleosomes by ELISA. http://www.jove.com/details.php?id=2593 doi: 10.3791/2593. J Vis Exp. 50 (2011).

Deligezer et al, Sequence-Specific Histone Methylation Is Detectable on Circulating Nucleosomes in Plasma. Clinical Chemistry 54(7), 1125-1131, 2008

Epigentek Group Inc, Methylamp™ Global DNA Methylation Quantification Kit, User Guide, Version 2.0802, 2009

Esteller, Cancer epigenomics: DNA methylomes and histone-modification maps Nature Reviews Genetics: 8, 286-298, 2007

Feinberg and Vogelstein, Hypomethylation distinguishes genes of some human cancers from their normal counterparts. Nature: 301, 89-92, 1983

Grutzmann et al, Sensitive Detection of Colorectal Cancer in Peripheral Blood by Septin 9 DNA Methylation Assay. PLoS ONE 3(11): e3759. doi:10.1371/journal.pone.0003759, 2008

Hervouet et al, Disruption of Dnmt1/PCNA/UHRF1 Interactions Promotes Tumorigenesis from Human and Mice Glial Cells PLoS ONE 5(6): e11333. doi:10.1371/journal.pone.0011333, 2010

Hua et al, Genomic analysis of estrogen cascade reveals histone variant H2A.Z associated with breast cancer progression. Molecular Systems Biology 4; Article number 188; doi:10.1038/msb.2008.25, 2008

Herranz and Esteller, DNA methylation and histone modifications in patients with cancer: potential prognostic and therapeutic targets. Methods Mol Biol. 361:25-62, 2007

Holdenrieder et al, Nucleosomes in serum of patients with benign and malignant diseases. Int. J. Cancer (Pred. Oncol.): 95, 114-120, 2001

*Holdenrieder et al, Nucleosomes in Serum as a Marker for Cell Death. Clin Chem Lab Med; 39(7), 596-605, 2001

Holdenrieder et al, Cell-Free DNA in Serum and Plasma: Comparison of ELISA and Quantitative PCR. Clinical Chemistry: 51(8), 1544-1546, 2005

Holdenreider and Stieber, Clinical use of circulating nucleosomes. Critical Reviews in Clinical Laboratory Sciences; 46(1): 1-24, 2009

Kapoor et al, The histone variant macroH2A suppresses melanoma progression through regulation of CDK8. Nature: 468, 1105-1111, 2010

Mansour et al, The Prognostic Significance of Whole Blood Global and Specific DNA Methylation Levels in Gastric Adenocarcinoma. PLoS ONE 5(12): e15585. doi: 10.1371/journal.pone.0015585, 2010

Moore et al, Genomic DNA hypomethylation as a biomarker for bladder cancer susceptibility in the Spanish Bladder Cancer Study: a case-control study. The Lancet Oncology: 9(4), 359-366, 2008

Ogoshi et al, Genome-wide profiling of DNA methylation in human cancer cells. Genomics: In Press, 2011

Pennings et al, DNA methylation, nucleosome formation and positioning. Briefings in functional genomics and proteomics: 3(4), 351-361, 2005

Rodriguez-Paredes and Esteller, Cancer epigenetics reaches mainstream oncology. Nature Medicine: 17(3), 330-339, 2011

Salgame et al, An ELISA for detection of apoptosis. Nucleic Acids Research, 25(3), 680-681, 1997

Sporn et al, Histone macroH2A isoforms predict the risk of lung cancer recurrence. Oncogene: 28(38), 3423-8, 2009

Stroud et al, 5-Hydroxymethylcytosine is associated with enhancers and gene bodies in human embryonic stem cells. Genome Biology: 12:R54, 2011

Tachiwana et al, Structures of human nucleosomes containing major histone H3 variants. Acta Cryst: D67, 578-583, 2011

Ting Hsiung et al, Global DNA Methylation Level in Whole Blood as a Biomarker in Head and Neck Squamous Cell Carcinoma. Cancer Epidemiology, Biomarkers & Prevention: 16(1), 108-114, 2007 van Nieuwenhuijze et al, Time between onset of apoptosis and release of nucleosomes from apoptotic cells: putative implications for systemic lupus erythematosus. Ann Rheum Dis; 62: 10-14, 2003

Vasser et al, Measurement of Global DNA Methylation. Genetic Engineering and Biotechnology News: 29(7), 2009

Whittle et al, The Genomic Distribution and Function of Histone Variant HTZ-1 during *C. elegans* Embryogenesis. PLoS Genet. 4(9): 1-17, 2008

Zee et al, Global turnover of histone post-translational modifications and variants in human cells Epigenetics & Chromatin. 3(22): 1-11, 2010

Zhang et al, Analysis of global DNA methylation by hydrophilic interaction ultra high-pressure liquid chromatography tandem mass spectrometry. Analytical Biochemistry: 413(2), 164-170, 2011

The invention claimed is:

1. A method for detecting the presence or degree of a particular DNA base selected from 5-methylcytosine and 5-hydroxymethylcytosine, the particular DNA base associated with a cell free nucleosome in a blood, serum or plasma sample which comprises the steps of:
   (i) separating cell free nucleosomes from the blood, serum or plasma sample by contacting the blood, serum or plasma sample with a first binding agent which binds to the cell free nucleosome;
   (ii) contacting the blood, serum or plasma sample cell free nucleosomes boundin step (i) with a second binding agent which binds to the particular DNA base;
   (iii) detecting the presence or degree of or quantifying the binding of said second binding agent to the particular DNA base in the blood, serum or plasma sample; and
   (iv) using the presence or degree of such binding as a measure of the presence of the particular DNA base associated with the cell free nucleosome in the blood, serum or plasma sample.

2. The method as defined in claim 1 wherein the first binding agent and/or the second binding agent is an antibody.

3. A method for detecting the presence or degree of a particular DNA base selected from 5-methylcytosine and 5-hydroxymethylcytosine, the particular DNA base associated with a cell free nucleosome in a blood, serum or plasma sample which comprises the steps of:
   (i) contacting the blood, serum or plasma sample with a first binding agent which binds to the particular DNA base;
   (ii) contacting the blood, serum or plasma sample particular DNA base bound in step (i) with a second binding agent which binds to cell free nucleosomes;
   (iii) detecting the presence or degree of or quantifying the binding of said second binding agent to the cell free nucleosomes nucleosome in the blood, serum or plasma sample; and
   (iv) using the presence or degree of such binding as a measure of the presence of the particular DNA base associated with the cell free nucleosome in the blood, serum or plasma sample.

4. The method as defined in claim 3 wherein the first binding agent and/or the second binding agent is an antibody.

\* \* \* \* \*